(12) United States Patent
Iwahori

(10) Patent No.: US 7,897,408 B2
(45) Date of Patent: Mar. 1, 2011

(54) METHOD FOR PRODUCING CDS-APOFERRITIN AND ZNS-APOFERRITIN COMPLEXES

(75) Inventor: Kenji Iwahori, Nara (JP)

(73) Assignee: Japan Science and Technology Agency, Saitama (JP)

( * ) Notice: Subject to any disclaimer, the term of this patent is extended or adjusted under 35 U.S.C. 154(b) by 433 days.

(21) Appl. No.: 12/066,078

(22) PCT Filed: Sep. 6, 2006

(86) PCT No.: PCT/JP2006/317671
§ 371 (c)(1),
(2), (4) Date: Mar. 6, 2008

(87) PCT Pub. No.: WO2007/032241
PCT Pub. Date: Mar. 22, 2007

(65) Prior Publication Data
US 2009/0233377 A1 Sep. 17, 2009

(30) Foreign Application Priority Data
Sep. 12, 2005 (JP) .................................. 2005-264326

(51) Int. Cl.
*G01N 21/76* (2006.01)
(52) U.S. Cl. ............. 436/172; 436/56; 436/86; 436/164; 436/166
(58) Field of Classification Search .................. None
See application file for complete search history.

(56) References Cited

U.S. PATENT DOCUMENTS

| | | | |
|---|---|---|---|
| 7,033,613 B2 | 4/2006 | Yamashita | |
| 7,105,323 B2 | 9/2006 | Yamashita | |
| 7,129,058 B2 | 10/2006 | Yamashita | |
| 2004/0158047 A1 | 8/2004 | Yamashita | |

FOREIGN PATENT DOCUMENTS

| | | |
|---|---|---|
| JP | 2003-7871 A | 1/2003 |
| JP | 2003-33191 A | 2/2003 |
| JP | 2003-113198 A | 4/2003 |
| JP | 3683265 B2 | 8/2005 |
| JP | 3703479 B2 | 10/2005 |

OTHER PUBLICATIONS

Iwahori et al. "Fabrication of CdS nanoparticles in the bio-template, apoferritin cavity by a slow chemical reaction system", J. Phys., Conf. Ser., 2007, v. 61, pp. 492-496.*

(Continued)

*Primary Examiner* — Yelena G Gakh
(74) *Attorney, Agent, or Firm* — Roberts Mlotkowski Safran & Cole P.C.

(57) ABSTRACT

First, an ammonium acetate solution and an acetate solution of a metal such as Cd or Zn are mixed, so as to form an ammonium complex of the metal. Next, an apoferritin solution, *listeria* apoferritin (*listeria* Dps) or their recombinant and thioacetic acid are added to the thus obtained reaction solution, which is maintained at a pH of from 4.0 to 9.0. By allowing the reaction solution to stand for 12 hours or more, a complex of a nanoparticle including CdS or ZnS and apoferritin or *listeria* Dps is produced.

12 Claims, 20 Drawing Sheets

(a) FERRITIN (b) LISTERIA FERRITIN

| | APOFERRITIN | LISTERIA APOFERRITIN |
|---|---|---|
| DIAMETER | 12nm | 9nm |
| CAVITY DIAMETER | 7nm | 4nm |
| MOLECULAR WEIGHT | 450kDa | 240kDa |
| NUMBER OF SUB-UNITS | 24 | 12 |

OTHER PUBLICATIONS

Yamashita et al. "Fabrication of CdS nanoparticles in the bio-template, apoferritin cavity by a slow chemical reaction system", J. Physics, 2007, v. 61, pp. 492-496.*

Kim K. W. Wong and Stephen Mann, "Biomimetic Synthesis of Cadmium Sulfide-Ferritin Nanocomposites", Advanced Materials, 1996, vol. 8, No. 11, p. 928-931.

Kenji Iwahori, Keiko Yoshizawa, Masahiro Muraoka, and Ichiro Yamashita, "Fabrication of ZnSe Nanoparticles in the Apoferritin Cavity by Designing a Slow Chemical Reaction System", Inorganic Chemistry, 2005, vol. 44, No. 18, p. 6393-6400.

Ichiro Yamashita, Junko Hayashi, and Masahiko Nara, "Bio-template Synthesis of Uniform CdSe Nanoparticles Using Cage-shaped Protein, Apoferritin", Chemistry Letters, 2004, vol. 33, No. 9, p. 1158-1159.

International Search Report for PCT/JP2006/317671 mailed Nov. 28, 2006.

Iwahori, K.; Enomoto, T.; Furusho, H.; Miura, A.; Nishio, K.; Mishima, Y.; & Yamashita, I., "Cadmium Sulfide Nanoparticle Synthesis in Dps Protein from *Listeria innocua*", Chem. Mater., 2007, vol. 19, No. 13, pp. 3105-3111.

Ilari, A.; Latella, M. C.; Ceci, P.; Ricacchi, F.; Su, M.; Giangiacomo, L.; et al., "The Unusual Intersubunit Ferroxidase Center of *Listeria innocua* Dps Is Required for Hydrogen Peroxide Detoxification but Not for Iron Uptake. A Study with Site-Specific Mutants", Biochemistry, 2005, vol. 44, No. 15, pp. 5579-5587.

* cited by examiner

|  | APOFERRITIN | LISTERIA APOFERRITIN |
|---|---|---|
| DIAMETER | 12nm | 9nm |
| CAVITY DIAMETER | 7nm | 4nm |
| MOLECULAR WEIGHT | 450kDa | 240kDa |
| NUMBER OF SUB-UNITS | 24 | 12 |

FIG. 7
(a) S source: THIOUREA
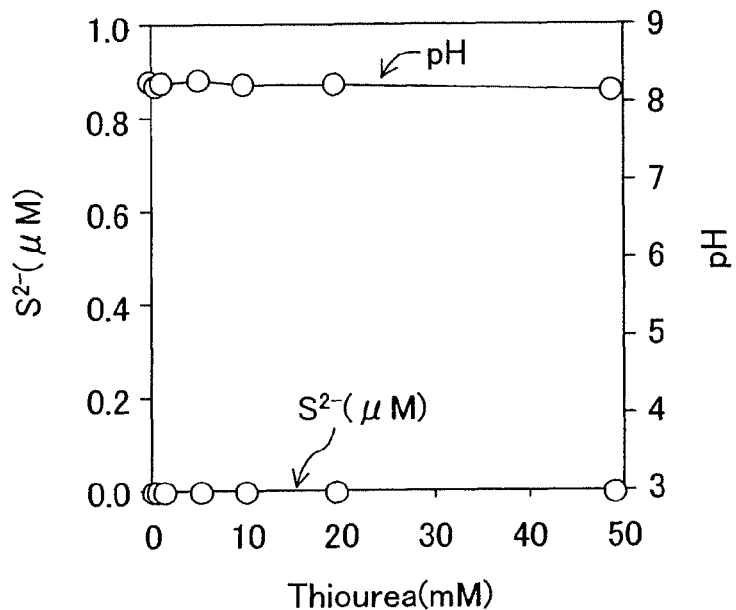
(b) S source: THIOACETIC ACID
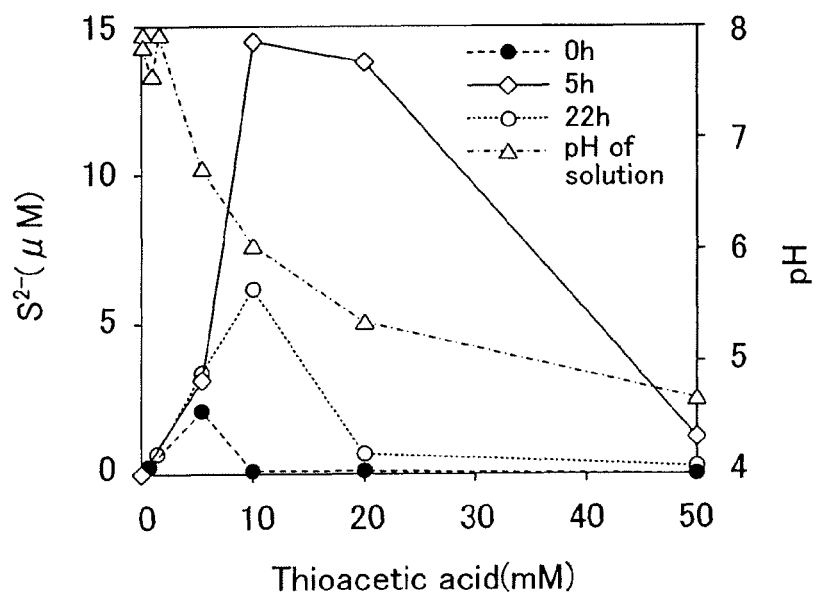

FIG. 8
POSITIVE ION
M:Cd
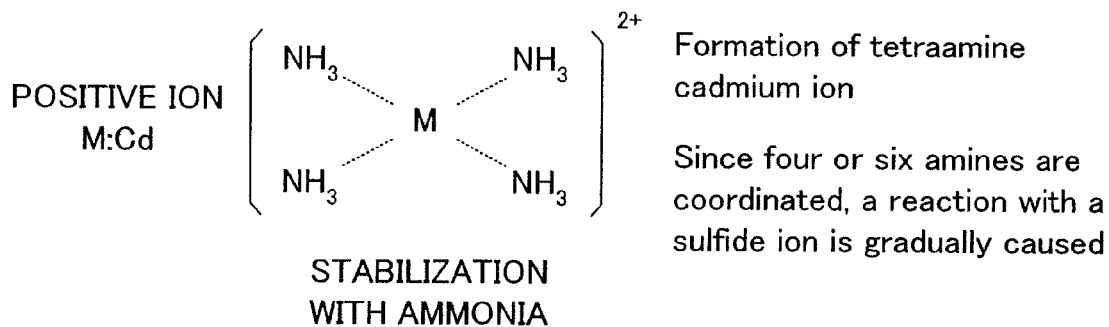
STABILIZATION
WITH AMMONIA
Formation of tetraamine cadmium ion
Since four or six amines are coordinated, a reaction with a sulfide ion is gradually caused
NEGATIVE ION
$S^{2-}$
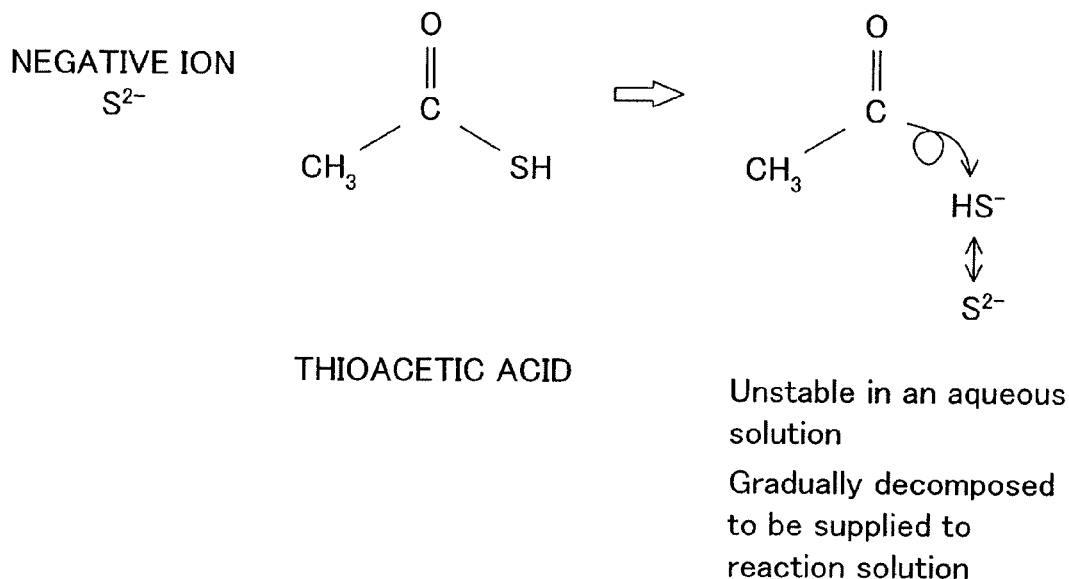
THIOACETIC ACID
Unstable in an aqueous solution
Gradually decomposed to be supplied to reaction solution (a)

(b)

| REAGENT | END CONCENTRATION |
|---|---|
| AMMONIUM ACETATE | 40mM |
| AMMONIA WATER | 0mM~100mM |
| ZINC ACETATE | 0.1mM~10mM |
| THIOACETIC ACID | 0.1mM~100mM |
| APOFERRITIN | 0.3mg/mL~1.0mg/mL |

(a)
```
S21: Mix ammonium acetate solution, ammonia water, cadmium acetate solution and listeria apoferritin solution
   ↓
S22: Allow to stand for 10 minutes (for forming ammonium complex)
   ↓
S23: Add thioacetic acid
   ↓
S24: Allow to stand for 12 hours or more (for forming ZnS-listeria apoferritin complex)
```

(b)

| REAGENT | END CONCENTRATION |
|---|---|
| AMMONIUM ACETATE | 40mM |
| AMMONIA WATER | 0mM~100mM |
| CADMIUM ACETATE | 1mM~5mM |
| THIOACETIC ACID | 4.0mM~10mM |
| LISTERIA APOFERRITIN | 0.3mg/mL~1.0mg/mL |

(pH4.0~9.0)

(c)

| CONDITIONS FOR PRODUCING CdS-LISTERIA FERRITIN | |
|---|---|
| AMMONIUM ACETATE | 40 mM |
| AMMONIA WATER | 0-100 mM |
| CADMIUM ACETATE | 2-5 mM |
| THIOACETIC ACID | 2-10 mM |
| LISTERIA APOFERRITIN | 0.3mg/mL-1mg/mL |
| | |
| TEMPERATURE | 0°C-15°C |

(a)

(b)

| REAGENT | END CONCENTRATION |
|---|---|
| AMMONIUM ACETATE | 40mM |
| AMMONIA WATER | 0mM~100mM |
| ZINC ACETATE | 0.5mM~5.0mM |
| THIOACETIC ACID | 0.5mM~50mM |
| LISTERIA APOFERRITIN | 0.3mg/mL~1.0mg/mL |

(pH4.0~9.0)

(c)

| CONDITIONS FOR PRODUCING ZnS-LISTERIA FERRITIN | |
|---|---|
| AMMONIUM ACETATE | 40 mM |
| AMMONIA WATER | 0-100 mM |
| ZINC ACETATE | 2-5 mM |
| THIOACETIC ACID | 2-5 mM |
| LISTERIA APOFERRITIN | 0.3mg/mL-1mg/mL |
| | |
| TEMPERATURE | 0°C-15°C |

CdS-Fer8 FLUORESCENCE SPECTRUM

FIG. 19
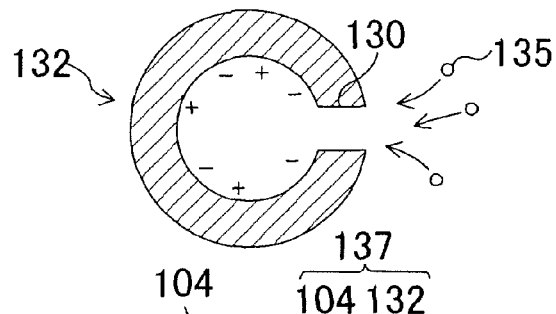
(a)
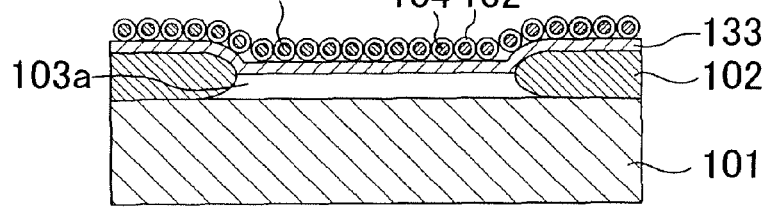
(b)
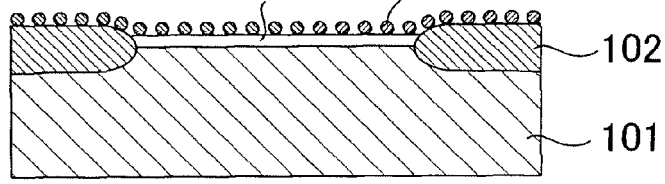
(c)
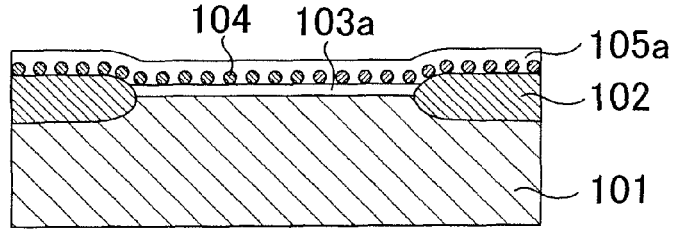
(d)
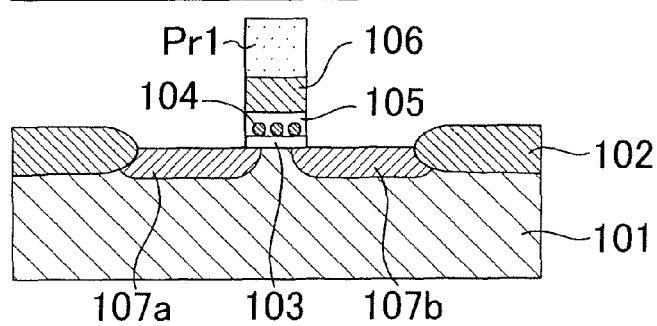
(e)
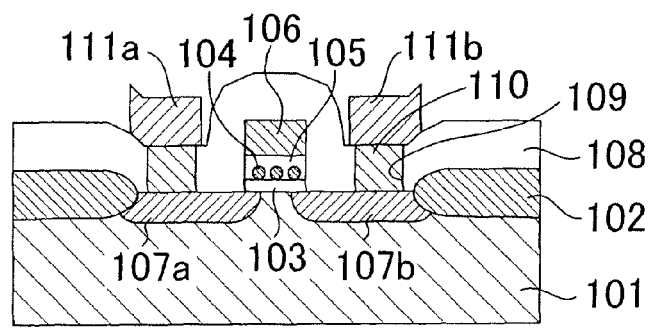
(f)

METHOD FOR PRODUCING CDS-APOFERRITIN AND ZNS-APOFERRITIN COMPLEXES

TECHNICAL FIELD

The present invention relates to a nanoparticle-protein complex and a method for producing the same.

BACKGROUND OF THE INVENTION

These days, earnest attention is being paid all over the world to nanotechnology for constructing a structure of a nanometer size. As one of the nanotechnology, an attempt is being made to form a metal nanoparticle by using, as a die, a protein in the shape of a spherical shell or a bar. Examples of the protein used in the so-called bio-nanoprocess are apoferritin, *listeria* ferritin and DNA binding protein.

FIG. 1 is a diagram for showing the characteristics of ferritin (apoferritin) and *listeria* ferritin (*listeria* apoferritin). Ferritin is a spherical shell-shaped protein included in a large amount in a liver, a spleen and a heart of a mammal with a diameter of approximately 12 nm (in a case of a horse), and 24 monomer sub-units 3 each including 175 amino acids together form one protein molecule. One protein molecule has a molecular weight of 480 kDa. The ferritin has, in vivo, a core 1 of iron oxide with a diameter of 7 nm at most within a shell 2 of the protein. Ferritin from which the iron oxide core 1 has been slipped off is designated as apoferritin.

On the other hand, the *listeria* ferritin is a Dps-like protein derived from *Listeria monocytogenes*, includes 12 monomer sub-units 9 and is in the shape of a spherical shell with a diameter of approximately 9 nm. In the *listeria* ferritin, a cavity where a core 6 of iron oxide can be held is formed within a shell 7 in the same manner as in the apoferritin, and the cavity has a diameter of approximately 4 nm. *Listeria* ferritin from which the tin oxide core 6 has been slipped off is designated as *listeria* apoferritin.

In the apoferritin, a core made of any of various metals can be formed instead of the iron oxide core. Therefore, complexes each composed of a nanoparticle of any of various metals such as cobalt (Co), manganese (Mn) and nickel (Ni) and the apoferritin have been conventionally produced. Also the *listeria* ferritin can be used in forming a nanoparticle of any of various metals.

Patent Document 1: Japanese Laid-Open Patent Publication No. 2003-113198

SUMMARY OF THE INVENTION

In the conventional technique, although a nanoparticle of a metal or a metal oxide can be produced, a nanoparticle of a compound semiconductor composed of two or more kinds of compounds cannot be produced. Therefore, examinations have been made to hold a nanoparticle of a semiconductor in the cavity of apoferritin. In a nanoparticle of a compound semiconductor, light emission through excitation is regarded as one standard of high crystallinity. A semiconductor nanoparticle with high crystallinity is necessary as a material of a semiconductor device but a nanoparticle made of a compound semiconductor and capable of emitting light cannot be produced by employing the bio-nanoprocess.

An object of the invention is producing a nanoparticle made of a compound semiconductor and capable of emitting light.

The nanoparticle-protein complex of this invention includes a shell that contains a plurality of monomer sub-units and has a cavity inside and a nanoparticle that is formed within the shell, is made of a compound semiconductor and emits fluorescence when excited.

Therefore, the nanoparticle-protein complex can be used not only in fabrication of a semiconductor device utilizing a quantum effect of a nanoparticle of a semiconductor but also in a labeling method for a biogenic substance by utilizing the fluorescence.

As the protein having a cavity, a ferritin-family protein such as apoferritin or *listeria* apoferritin, or a recombinant thereof is preferably used.

Examples of the material for the nanoparticle are CdS, ZnS and the like, that is, group II-VI compound semiconductors. The diameter of the nanoparticle is approximately 7 nm or less in using apoferritin and approximately 4 nm or less in using *listeria* apoferritin.

The method for producing a nanoparticle-protein complex of this invention includes the steps of (a) forming an ammonium complex of a metal in an aqueous solution; and (b) mixing a solution of a protein having a cavity inside and thioacetic acid in the aqueous solution, whereby forming, within the cavity of the protein, a nanoparticle made of a sulfide of the metal.

Thus, formation of the metal sulfide outside the protein is prevented by forming the ammonium complex, and $S^{2-}$ ions are gradually released from the thioacetic acid, and therefore, it seems that the metal sulfide with high crystallinity can be formed within the protein. The protein is preferably a ferritin-family protein such as apoferritin or *listeria* apoferritin, and the metal is preferably Cd or Zn.

When the nanoparticle-protein complex produced by the aforementioned method is used, a semiconductor memory using the nanoparticle can be realized, and a biogenic substance or the like can be labeled by using fluorescence emitted by the nanoparticle.

In this manner, the nanoparticle-protein complex produced by the method of this invention can be used in any of various fields including fabrication of a semiconductor device and labeling of a biogenic substance or the like.

BRIEF DESCRIPTION OF DRAWINGS

FIG. 7A is a diagram for showing the $S^{2-}$ ion concentration and the pH of a reaction solution in using thiourea and FIG. 7B is a diagram for showing the $S^{2-}$ ion concentration and the pH of a reaction solution in using thioacetic acid.

FIG. 8 is a diagram for explaining the reaction mechanism of a method for producing a CdS-apoferritin complex of Embodiment 1.

FIG. 12A is a flowchart of a method for producing a compound semiconductor-*listeria* apoferritin complex according to Embodiment 3 of the invention, FIG. 12B is a diagram for showing the end concentrations of respective reagents and FIG. 12C is a diagram for showing the end concentrations of respective reagents employed in a method for producing a compound semiconductor-*listeria* apoferritin complex according to a modification of Embodiment 3.

FIGS. 19A through 19F are cross-sectional views for showing a method for fabricating the semiconductor device of Embodiment 6.

Figure 1:
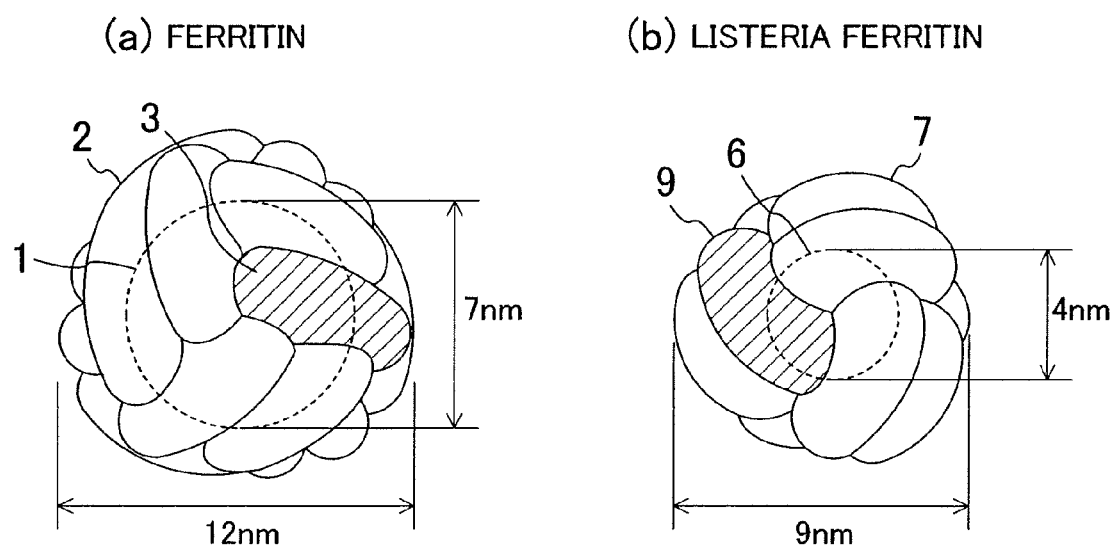
FIG. 1 is a diagram for showing the characteristics of ferritin (apoferritin) and *listeria* ferritin.

DESCRIPTION OF REFERENCE NUMERALS 1, 6, 11 core
2, 7, 12 shell
3, 9, 13 monomer sub-unit
101 semiconductor substrate
102 isolation insulating film
103 tunnel insulating film
103a, 105a SiO$_2$ film
104 nanoparticle
105 insulating film
106 control gate
107a source region
107b drain region
108 interlayer insulating film
109 contact hole
110 tungsten plug
111a, 111b Al interconnection
120 semiconductor device
130 channel
132 apoferritin
135 sulfide ion (metal ion)
137 nanoparticle-apoferritin complex

DETAILED DESCRIPTION OF THE INVENTION

Preferred embodiments of the invention will now be described with reference to the accompanying drawings.

Embodiment 1

Figure 2:
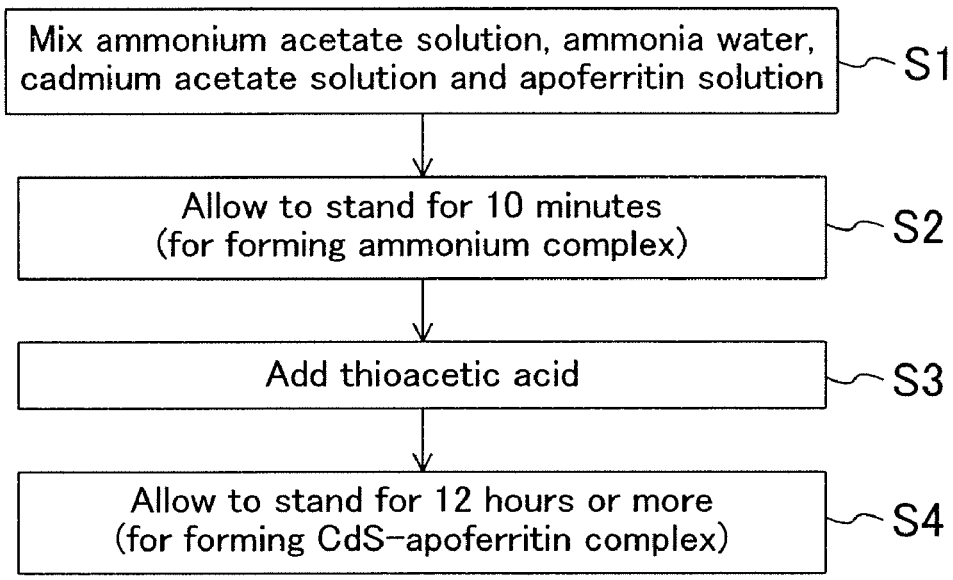
FIG. 2A is a flowchart of a method for producing a compound semiconductor-apoferritin complex according to Embodiment 1 of the invention and FIG. 2B is a diagram for showing end concentrations of respective reagents.

FIG. 2A is a flowchart of a method for producing a compound semiconductor-apoferritin complex according to Embodiment 1 of the invention and FIG. 2B is a diagram for showing the end concentrations of respective reagents. In this embodiment, a method for forming a nanoparticle of cadmium sulfide (CdS) within apoferritin is described.

First, in step S1 of FIG. 2A, an ammonium acetate solution and a cadmium acetate solution are mixed. Specifically, 1 M of ammonium acetate, 1 M of ammonia water and 100 mM of a cadmium acetate solution are mixed in 300 mL of pure water. The respective reagents are mixed so that the end concentration of ammonium acetate can be 40 mM, the end concentration of ammonia can be 7.5 mM, 37.5 mM or 75 mM and the end concentration of cadmium acetate can be 1 mM. Thereafter, an apoferritin solution is added to the thus obtained reaction solution. Specifically, an apoferritin solution in an appropriate concentration is added to the reaction solution so as to attain an end concentration of, for example, 0.3 mg/mL. It is noted that the reagents used in the method of this embodiment are not limited to those herein exemplified.

Next, in step S2, the reaction solution prepared in step S1 is allowed to stand for 10 minutes at room temperature. Thus, an ammonium complex of cadmium is obtained.

Subsequently, in step S3, thioacetic acid (C$_2$H$_4$OS) is added to the reaction solution. Specifically, thioacetic acid is added to the reaction solution so as to attain an end concentration of 1 mM. It is noted that the apoferritin used in this embodiment is apoferritin derived from a horse spleen. Also, this apoferritin includes two kinds of monomer sub-units, that is, an L sub-unit and an H sub-unit.

Thereafter, in step S4, the reaction solution is allowed to stand for 12 hours or more at room temperature, so as to produce a CdS-apoferritin complex. At this point, pH is set to approximately 4.0 or more and 9.0 or less.

The end concentrations of the respective reagents are not limited to those mentioned above. Exemplified ranges of the end concentrations of the respective reagents are listed in FIG. 2B. However, even when the end concentration of the apoferritin in the reaction solution is out of the range from 0.3 mg/mL to 1 mg/mL, a CdS-apoferritin complex can be produced. Also, the concentration of ammonium acetate is not limited to 40 mM. Furthermore, the reaction time employed in step S4 may be approximately 24 hours.

Figure 3:
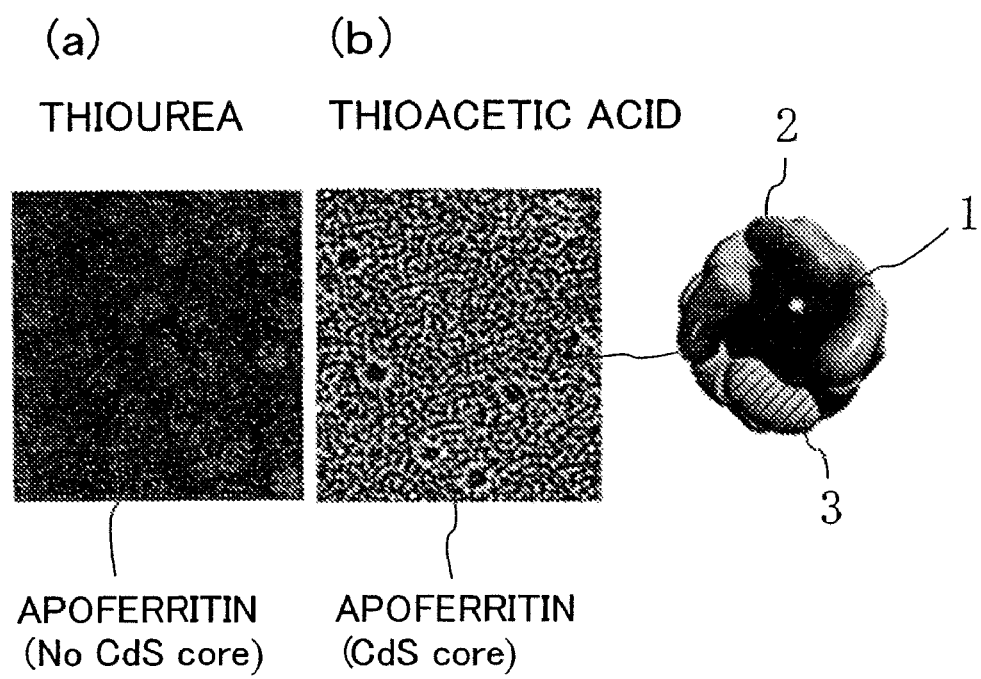
FIG. 3A is a transmission electron microscope (TEM) photograph of apoferritin present in a reaction solution in using thiourea as a sulfur source and FIG. 3B is a TEM photograph of apoferritin present in a reaction solution in using thioacetic acid as a sulfur source.

FIG. 3A is a transmission electron microscope (TEM) photograph of apoferritin present in a reaction solution in using thiourea as a sulfur source, and FIG. 3B is a TEM photograph of apoferritin present in a reaction solution in using thioacetic acid as the sulfur source. Also, FIG. 4 is a TEM photograph of CdS-apoferritin complexes produced with the ammonia concentration in the reaction solution changed.

As shown in FIG. 3B, it is understood that a core of CdS (observed as a black circle in the photograph) is formed within the apoferritin by the method of this embodiment. On the contrary, when thiourea is used as the sulfur source instead of thioacetic acid, a core of CdS is minimally formed in the apoferritin. This difference will be examined later.

Figure 4:
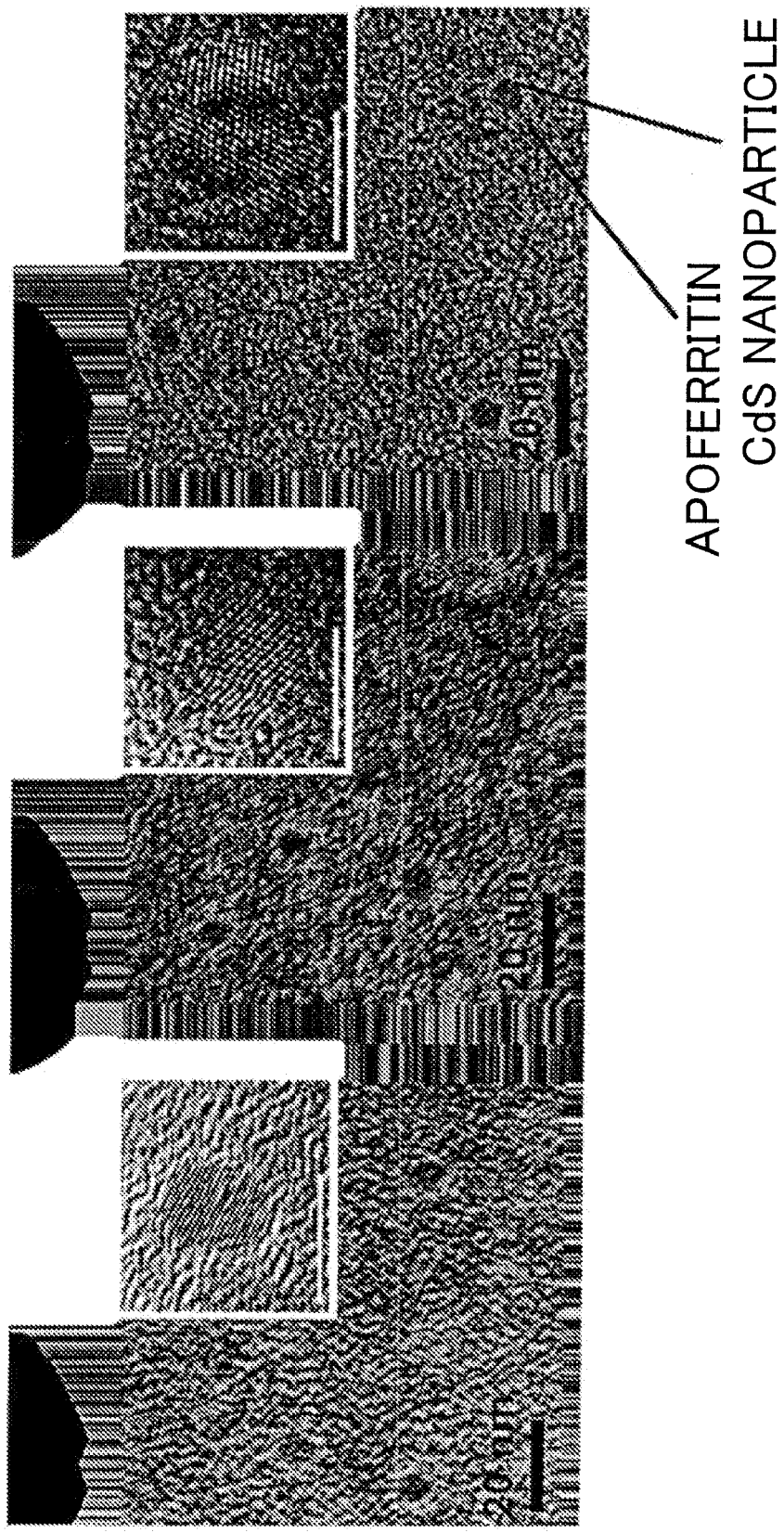
FIG. 4 is a TEM photograph of a CdS-apoferritin complex obtained by changing an ammonia concentration in a reaction solution.

Furthermore, it is understood from the result shown in FIG. 4 that CdS-apoferritin complexes with difference particle sizes of nanoparticles can be formed by changing the ammonia concentration in the reaction solution between 7.5 mM and 75 mM.

Figure 5:
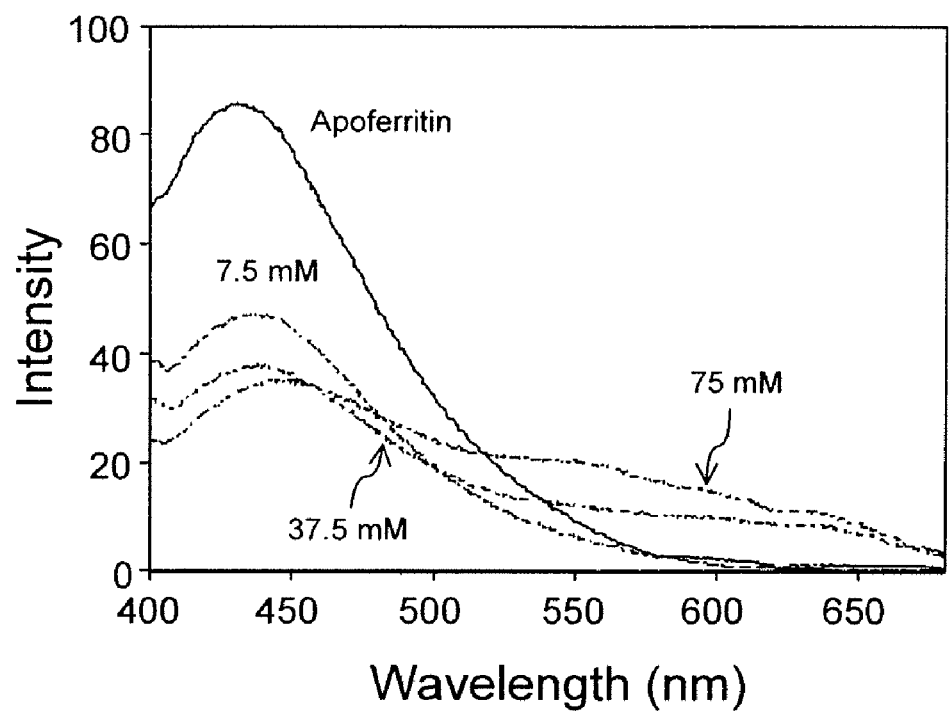
FIG. 5 is a diagram of a fluorescence spectrum of a CdS-apoferritin complex.

FIG. 5 is a diagram for showing the fluorescence spectrum of a CdS-apoferritin complex. This drawing shows the fluorescence spectrum of a CdS-apoferritin obtained through excitation with light of a wavelength of 350 nm in a reaction solution including the CdS-apoferritin complex in a concentration of 0.5 mg/mL. In this drawing, a peak appearing in the vicinity of a wavelength of 440 nm through 450 nm seems to be fluorescence derived from the apoferritin. Also, particularly in the cases where the ammonia concentration is 37.5 mM and 75 mM, fluorescence probably derived from a CdS nanoparticle is observed in the vicinity of wavelengths of 560 nm, 610 nm and 640 nm. When a reaction solution irradiated with the excitation light is visually observed, a reaction solution including the apoferritin alone looks blue, and the color of the reaction solution is changed to be closer to red as the ammonia concentration is increased.

Figure 6:
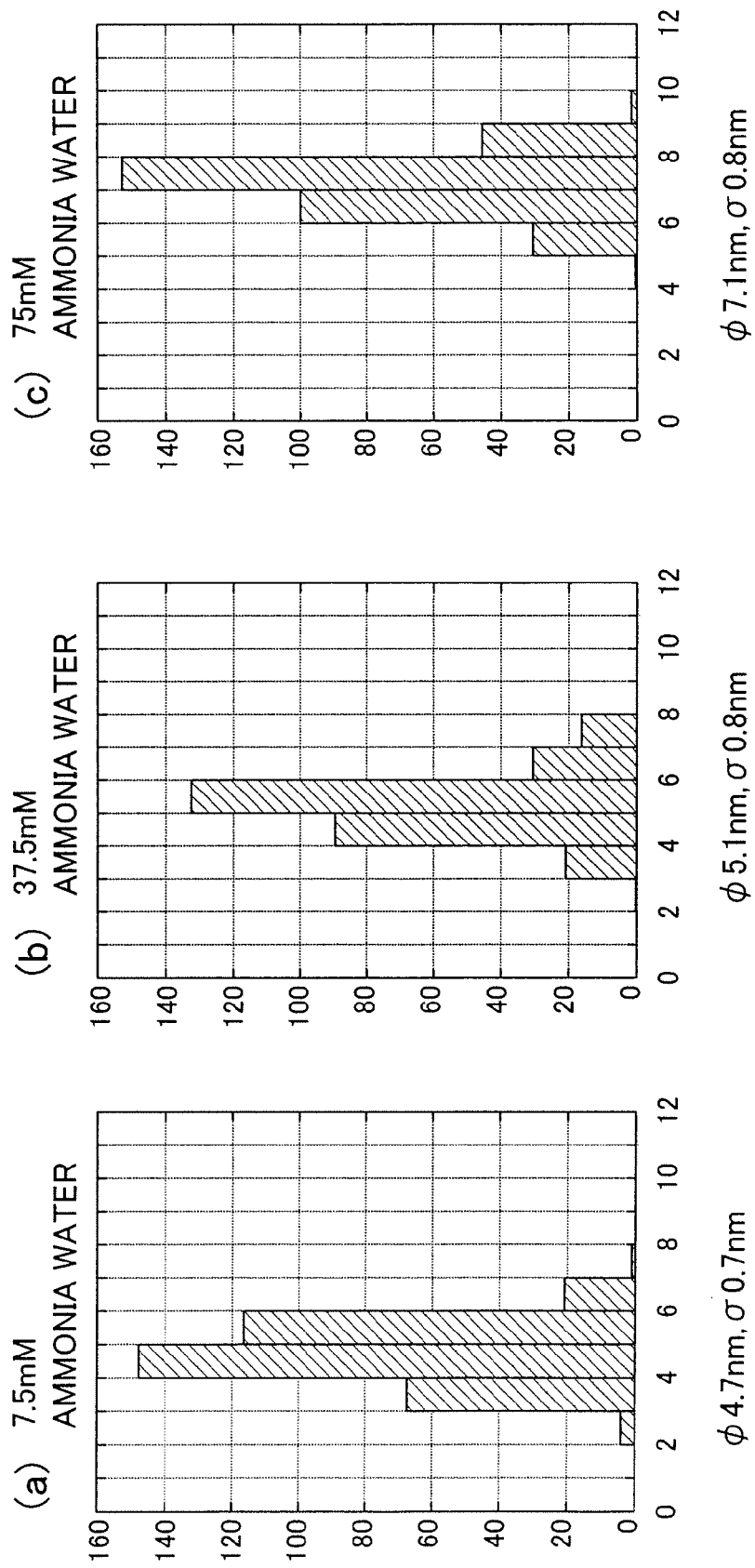
FIGS. 6A through 6C are diagrams for showing measured particle sizes of CdS nanoparticles formed in apoferritin under various conditions.

At this point, the present inventors have examined why the peak of the fluorescence wavelength is different among CdS-apoferritin complexes formed in reaction solutions with different ammonia concentrations. FIGS. 6A through 6C are diagrams for showing measured particle sizes of CdS nanoparticles formed within apoferritin under various conditions. These results are obtained by analyzing TEM images with particle size analyzing software.

As a result, as shown in FIG. 6A, it is found that when the ammonia concentration is 7.5 mM, the average particle size of CdS nanoparticles is 4.7 nm and the standard deviation σ is 0.7 nm. Also, as shown in FIG. 6B, it is found that when the ammonia concentration is 37.5 mM, the average particle size of CdS nanoparticles is 5.1 nm and the standard deviation σ is 0.8 nm. Furthermore, as shown in FIG. 6C, it is found that when the ammonia concentration is 75 mM, the average particle size of CdS nanoparticles is 7.1 nm and the standard deviation σ is 0.8 nm. It is understood from these results that CdS nanoparticles with different particle sizes can be formed by controlling the ammonia concentration in the reaction solution. Moreover, it is found that nanoparticles with uniform particle sizes can be obtained in the method of this embodiment as compared with another method for forming nanoparticles.

Specifically, a CdS-apoferritin complex produced by the method of this embodiment includes, as shown in FIG. 3B, a large number of (24) monomer sub-units 3, and includes a shell 2 that has a cavity (holding portion) therein and a core (nanoparticle) 1 that is made of CdS formed within the cavity of the shell and emits fluorescence when excited.

Next, the hypothesis of a reason why a CdS-apoferritin complex can be produced by the method of this embodiment will be described.

FIG. 7A is a diagram for showing the $S^{2-}$ ion concentration and the pH of a reaction solution in using thiourea and FIG. 7B is a diagram for showing the $S^{2-}$ ion concentration and the pH of a reaction solution in using thioacetic acid. FIG. 8 is a diagram for explaining the reaction mechanism of the method for producing a CdS-apoferritin complex of this embodiment. It is noted that a reaction solution including no Cd ion is used in the measurement shown in FIGS. 7A and 7B.

As shown in FIG. 7A, when thiourea is used as the sulfur source, no $S^{2-}$ ions are found in the reaction solution in any concentration, and the pH of the reaction solution is not affected by the concentration of the thiourea. On the contrary, as shown in FIG. 7B, when thioacetic acid is used as the sulfur source, the $S^{2-}$ ion concentration is gradually increased after adding the thioacetic acid, becomes high after 5 hours and is lowered after 22 hours. The pH of the reaction solution is changed in accordance with the concentration of the thioacetic acid. Furthermore, the $S^{2-}$ ion concentration is the highest when the concentration of thioacetic acid is 10 through 20 mM. Since a CdS-apoferritin complex is minimally produced in using thiourea, it seems that $S^{2-}$ ions are necessary for the production of a CdS-apoferritin complex.

Moreover, in the case where no ammonium ion is added to a reaction solution, a CdS nanoparticle is formed outside apoferritin, and therefore, it seems that cadmium stabilized by forming a complex with an ammonium ion seems to be preferred for forming a CdS-apoferritin complex. In other words, a CdS-apoferritin complex is produced by the method of this embodiment probably because thioacetic acid more unstable than thiourea is gradually decomposed within the aqueous solution so as to supply $S^{2-}$ ions and precipitation of CdS outside the apoferritin is prevented by forming a tetraamine cadmium ion by adding an ammonium ion.

In step S1 of FIG. 2A, a CdS-apoferritin complex can be produced even when a solution including an ammonium ion and an acetic acid ion, such as acetic acid including an ammonium ion, is used instead of the ammonium acetate solution.

Furthermore, although the reaction solution is allowed to stand at room temperature in step S2 or step S4 of FIG. 2A, the complex or the CdS-apoferritin complex can be obtained by allowing it to stand at a temperature other than room temperature.

Although thioacetic acid is most preferred as the sulfur source, a CdS-apoferritin complex can be produced by using ammonium sulfide $((NH_4)_2S)$, thiosulfate $(K_2S_2O_3$ or $Na_2S_2O_3)$ or the like instead of the thioacetic acid. A CdS-apoferritin complex can be slightly produced by using thiourea as far as the reaction time is increased, but the number of complexes thus produced is small and hence this method is not practical.

Moreover, although the apoferritin derived from a horse spleen is used in the above-described method, apoferritin derived from another organ (such as a heart or a liver) may be used, or even when apoferritin derived from another animal is used, a CdS-apoferritin complex can be produced in a method similar to the method of this embodiment.

It is noted that the CdS-apoferritin complex of this embodiment can be used in any of various fields including a semiconductor memory using CdS nanoparticles and a marker using the fluorescent characteristic.

Embodiment 2

Figure 9:
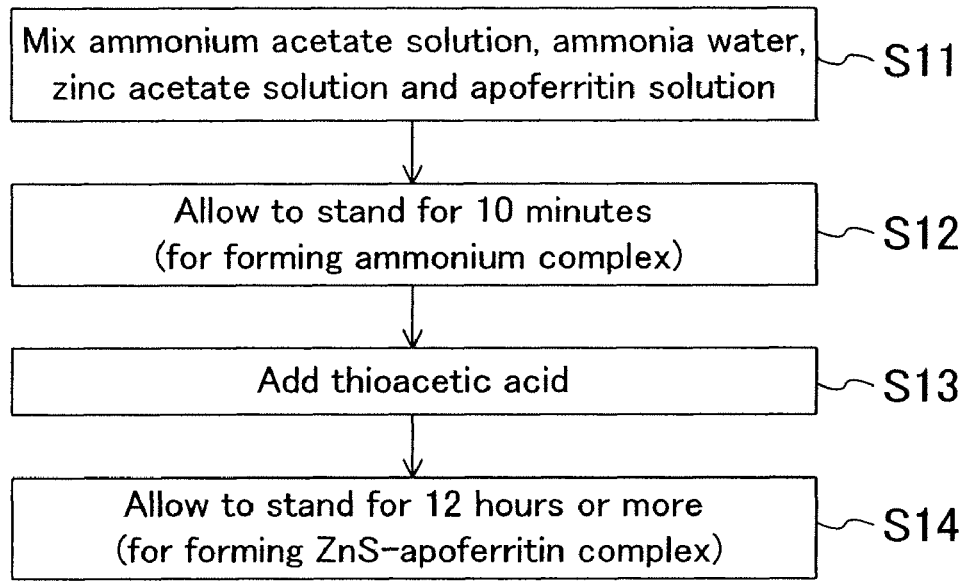
FIG. 9A is a flowchart of a method for producing a compound semiconductor-apoferritin complex according to Embodiment 2 of the invention and FIG. 9B is a diagram for showing the end concentrations of respective reagents.

FIG. 9A is a flowchart of a method for producing a compound semiconductor-apoferritin complex according to Embodiment 2 of the invention and FIG. 9B is a diagram for showing the end concentrations of respective reagents. In this embodiment, a method for forming a nanoparticle of zinc sulfide (ZnS) within apoferritin will be described.

First, in step S11 of FIG. 9A, an ammonium acetate solution and a zinc acetate solution are mixed. Specifically, 1 M of ammonium acetate, 1 M of ammonia water and 100 mM of a zinc acetate solution are mixed in 300 mL of pure water. The respective reagents are mixed so that the end concentration of ammonium acetate can be 40 mM, the end concentration of ammonia can be 7.5 mM through 75 mM and the end concentration of zinc acetate can be 1 mM. Thereafter, an apoferritin solution is added to the thus obtained reaction solution. Specifically, an apoferritin solution in an appropriate concentration is added so as to attain an end concentration of, for example, 0.3 mg/mL. It is noted that the concentrations of the reagents used in the method of this embodiment are not limited to those herein exemplified.

Next, in step S12, the reaction solution prepared in step S11 is allowed to stand for 10 minutes at room temperature. Thus, an ammonium complex of zinc is formed.

Subsequently, in step S13, thioacetic acid is added to the reaction solution. Specifically, thioacetic acid is added to the reaction solution so as to attain an end concentration of 10 mM. It is noted that the apoferritin used in this embodiment is apoferritin derived from a horse spleen.

Thereafter, in step S14, the reaction solution is allowed to stand for 12 hours or more at room temperature, so as to produce a ZnS-apoferritin complex. At this point, the pH is set to approximately 4.0 or more and 9.0 or less. The ZnS formed within the apoferritin in this case may be partly a zinc sulfide other than ZnS such as $ZnS_2$ depending upon the condition. The reaction time employed in step S14 may be approximately 24 hours.

The end concentrations of the reagents are not limited those mentioned above. Exemplified ranges of the concentrations of the respective reagents are listed in FIG. 9B. However, even when the end concentration of the apoferritin in the reaction solution is out of the range from 0.3 mg/mL to 1 mg/mL, a ZnS-apoferritin complex can be produced. Also, the concentration of ammonium acetate is not limited to 40 mM.

Figure 10:
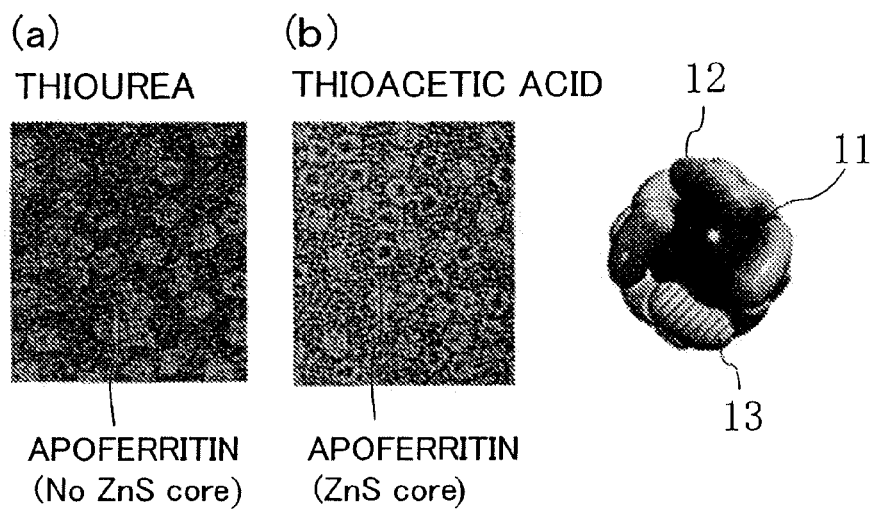
FIG. 10A is a transmission electron microscope (TEM) photograph of apoferritin present in a reaction solution in using thiourea as a sulfur source and FIG. 10B is a TEM photograph of apoferritin present in a reaction solution in using thioacetic acid as a sulfur source.

FIG. 10A is a transmission electron microscope (TEM) photograph of apoferritin present in a reaction solution in using thiourea as a sulfur source, and FIG. 10B is a TEM photograph of apoferritin present in a reaction solution in using thioacetic acid as the sulfur source.

As shown in FIG. 10B, it is understood that a core made of a zinc sulfide including ZnS can be formed within the apoferritin by the method of this embodiment. On the contrary, when thiourea is used as the sulfur source instead of thioacetic acid, a core of a zinc sulfide is minimally formed in the apoferritin. Furthermore, even when the ammonia concentration in the reaction solution is changed between 1.0 mM and 100 mM, a ZnS-apoferritin complex can be formed (not shown).

Figure 11:
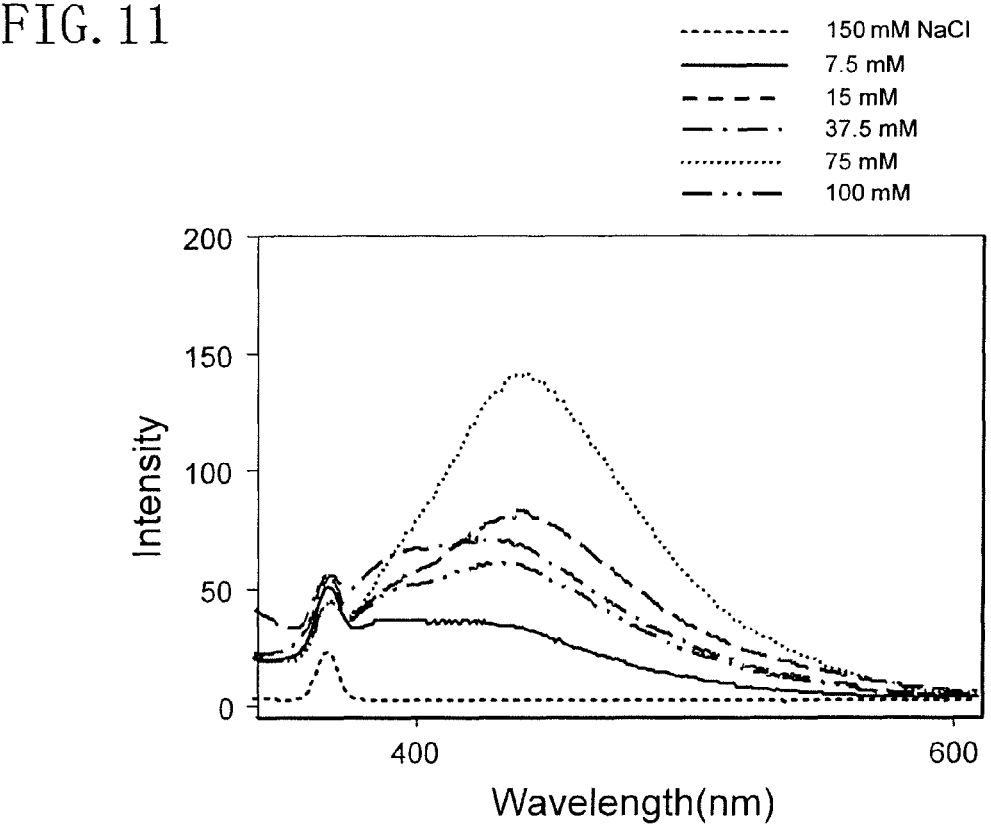
FIG. 11 is a diagram for showing a fluorescence spectrum of a ZnS-apoferritin complex.

FIG. 11 is a diagram of a fluorescence spectrum of a ZnS-apoferritin complex. This drawing shows the fluorescence spectrum obtained by exciting a ZnS nanoparticle with light of a wavelength of 325 nm within a reaction solution including the ZnS-apoferritin complex. In this drawing, a peak present in a region lower than a wavelength of 400 nm seems to be fluorescence not depending upon the ZnS nanoparticle through comparison with a blank sample of a 150 mM NaCl solution. When the ammonia concentration in the reaction solution is in the range from 7.5 mM to 100 mM, fluorescence probably derived from a ZnS nanoparticle is observed in a region of a wavelength of 400 nm through 500 nm. In particular, when the ammonia concentration in the reaction solution is in a range from 15 mM to 100 mM, stronger fluorescence is observed. The fluorescence derived from a ZnS nanoparticle visually looks blue, and quenching is minimally caused after long storage (of 1 year). Furthermore, in the same manner as in a CdS nanoparticle, the particle size of a ZnS nanoparticle is changed in accordance with the increase of the ammonia concentration in the reaction solution.

A ZnS-apoferritin complex produced by the method of this embodiment includes, as shown in FIG. 10B, a large number of (24) monomer sub-units 13, and includes a shell 12 that has a cavity inside and a core (nanoparticle) 11 that is made of ZnS formed within the cavity of the shell 12 and emits fluorescence when excited. It is noted that the ZnS-apoferritin complex of this embodiment can be used in any of various fields including a semiconductor memory using ZnS nanoparticles and a marker using the fluorescent characteristic.

Furthermore, although the reaction solution is allowed to stand at room temperature in step S12 or step S14 of FIG. 9A, the ammonium complex or the ZnS-apoferritin complex can be obtained by allowing it to stand at a temperature other than room temperature.

Although thioacetic acid is most preferred as the sulfur source, a ZnS-apoferritin complex can be produced by using ammonium sulfide $((NH_4)_2S)$, thiosulfate $(K_2S_2O_3$ or $Na_2S_2O_3)$ or the like instead of the thioacetic acid.

Moreover, although the apoferritin derived from a horse spleen is used in the above-described method, apoferritin derived from another organ (such as a heart or a liver) may be used, or a ZnS-apoferritin complex can be produced in a method similar to the method of this embodiment by using apoferritin derived from another animal.

Alternatively, a ZnS-apoferritin complex can be produced by using, instead of the ammonium acetate, a solution including an ammonium ion and an acetic acid ion, such as an acetate buffer including ammonia water.

Embodiment 3

FIG. 12A is a flowchart of a method for producing a compound semiconductor-apoferritin complex according to Embodiment 3 of the invention and FIG. 12B is a diagram for showing the end concentrations of respective reagents. In this embodiment, a method for forming a nanoparticle of CdS within *listeria* apoferritin will be described.

First, in step S21 of FIG. 12A, an ammonium acetate solution and a cadmium acetate solution are mixed. Specifically, 1 M of ammonium acetate, 1 M of ammonia water and 100 mM of a cadmium acetate solution are mixed in 300 mL of pure water. The respective reagents are mixed so that the end concentration of ammonium acetate can be 40 mM, the end concentration of ammonia can be 7.5 mM through 75 mM and the end concentration of cadmium acetate can be 1 mM. Thereafter, a *listeria* apoferritin solution is added to the thus obtained reaction solution. Specifically, a *listeria* apoferritin solution in an appropriate concentration is added so as to attain an end concentration of, for example, 0.3 mg/mL. It is noted that the concentrations of the reagents used in the method of this embodiment are not limited to those herein exemplified.

Next, in step S22, the reaction solution prepared in step S21 is allowed to stand for 10 minutes at room temperature. Thus, an ammonium complex of cadmium is formed.

Subsequently, in step S23, thioacetic acid is added to the reaction solution. Specifically, thioacetic acid is added to the reaction solution so as to attain an end concentration of 5 through 10 mM. It is noted that the *listeria* apoferritin used in this embodiment is a Dps-like protein derived from *Listeria monocytogenes* or its variant protein.

Thereafter, in step S24, the reaction solution is allowed to stand for 12 hours or more at room temperature, so as to produce a CdS-apoferritin complex. At this point, the pH is set to approximately 4.0 or more and 9.0 or less. The reaction solution is allowed to stand preferably at a temperature of 0° C. through 55° C.

The end concentrations of the reagents are not limited those mentioned above. Exemplified ranges of the concentrations of the respective reagents are listed in FIG. 12B. However, even when the end concentration of the *listeria* apoferritin in the reaction solution is out of the range from 0.3 mg/mL to 1 mg/mL, a CdS-*listeria* apoferritin complex can be obtained. Also, the concentration of ammonium acetate is not limited to 40 mM.

The CdS-*listeria* apoferritin complex produced by this method includes 12 monomer sub-units of *listeria* apoferritin, and includes a shell having a cavity inside and a nanoparticle of CdS formed within the cavity. The diameter of the nanoparticle is approximately 5 nm or less.

Modification of Embodiment 3

FIG. 12C is a diagram for showing the conditions for producing a compound semiconductor-*listeria* apoferritin complex according to a modification of Embodiment 3.

In a method of this modification, an ammonium acetate solution, a cadmium acetate solution, ammonia water and a *listeria* apoferritin solution are mixed in step S21 of FIG. 12A so as to attain end concentrations shown in FIG. 12C. At this point, the reaction temperature is set to 0 through 15° C. Particularly, the temperature is preferably approximately 4° C. Also, the concentration of the cadmium acetate solution is preferably higher than that in Embodiment 3.

Next, after allowing the reaction solution to stand for 10 minutes in step S22, thioacetic acid is added to the reaction solution so as to attain a concentration shown in FIG. 12A. At this point, the concentrations of the cadmium acetate and thioacetic acid are preferably hither than in the method of Embodiment 3.

Next, in step S24, the reaction solution is allowed to stand for 12 hours or more at a temperature of 0° C. or more and 15° C. or less, so as to produce a CdS-*listeria* apoferritin complex.

In this method, the forming ratio of a CdS nanoparticle in *listeria* apoferritin can be improved to approximately 100%.

Figure 13:
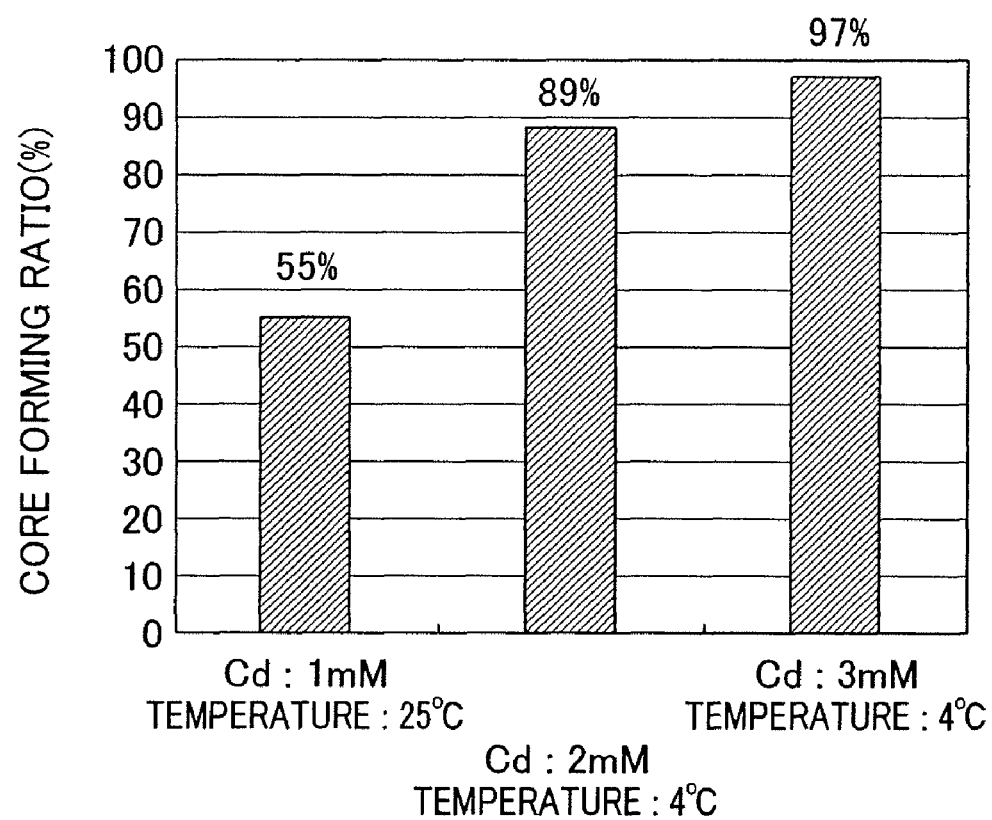
FIG. 13 is a diagram for showing a core forming ratio attained under various conditions for a method for producing a CdS-*listeria* apoferritin complex.

FIG. 13 is a diagram for showing core forming ratios attained by changing the conditions for producing a CdS-*listeria* apoferritin complex. It is understood from this result that the core forming ratio can be improved when the reaction is caused at 4° C. as compared with when it is caused at 25° C. and that the core forming ratio is higher at a low temperature when the concentration of the cadmium acetate (namely, the concentration of cadmium) in the reaction solution is higher. In particular, when the concentration of cadmium is 3 mM, the core forming ratio is substantially 100%. In the case where the concentration of cadmium is increased in the reaction caused at 25° C., CdS is more largely precipitated outside the *listeria* apoferritin, and hence, the core forming ratio is not improved. Therefore, it is presumed that CdS is gradually precipitated when the reaction is caused at a low temperature in a high cadmium concentration so as to improve the forming ratio of a nanoparticle within the *listeria* apoferritin.

According to this method, a CdS nanoparticle can be more definitely produced. Therefore, the cost for producing the nanoparticle can be lowered.

Embodiment 4

Figure 14:
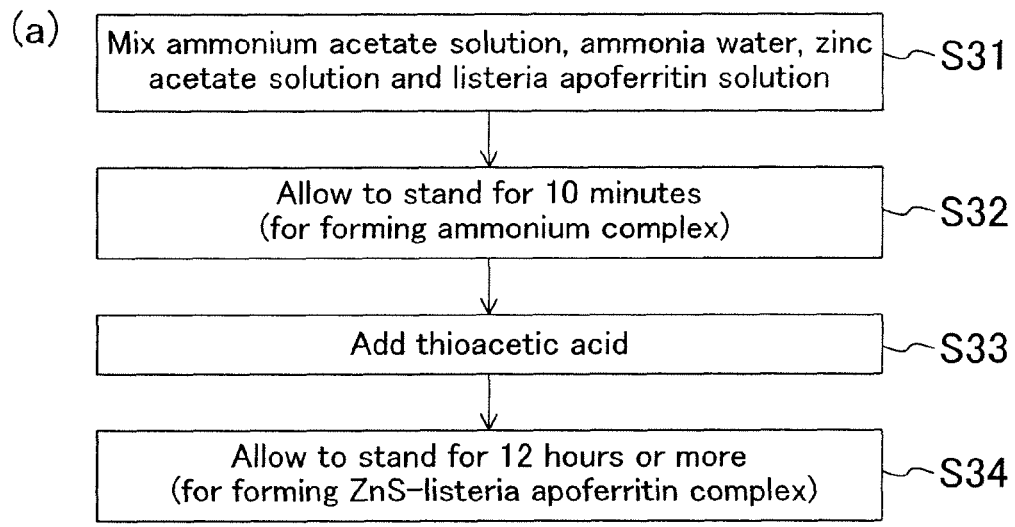
FIG. 14A is a flowchart of a method for producing a compound semiconductor-*listeria* apoferritin complex according to Embodiment 4 of the invention.
FIG. 14B is a diagram for showing the end concentrations of respective reagents and FIG. 14C is a diagram for showing the end concentrations of respective reagents employed in a method for producing a compound semiconductor-*listeria* apoferritin complex according to a modification of Embodiment 4.

FIG. 14A is a flowchart of a method for producing a compound semiconductor-*listeria* apoferritin complex according to Embodiment 4 of the invention and FIG. 14B is a diagram for showing the end concentrations of respective reagents. In this embodiment, a method for forming a nanoparticle of zinc sulfide (ZnS) within *listeria* apoferritin will be described.

First, in step S31 of FIG. 14A, an ammonium acetate solution and a zinc acetate solution are mixed. Specifically, 1 M of ammonium acetate, 1 M of ammonia water and 100 mM of a zinc acetate solution are mixed in 300 mL of pure water. The respective reagents are mixed so that the end concentration of ammonium acetate can be 40 mM, the end concentration of ammonia can be 10 mM and the end concentration of zinc acetate can be 1 mM. Thereafter, a *listeria* apoferritin solution is added to the thus obtained reaction solution. Specifically, a *listeria* apoferritin solution in an appropriate concentration is added so as to attain an end concentration of, for example, 0.3 mg/mL. It is noted that the concentrations of the reagents used in the method of this embodiment are not limited to those herein exemplified.

Next, in step S32, the reaction solution prepared in step S31 is allowed to stand for 10 minutes at room temperature. Thus, an ammonium complex of zinc is formed.

Subsequently, in step S33, thioacetic acid is added to the reaction solution. Specifically, thioacetic acid is added to the reaction solution so as to attain an end concentration of 10 mM.

Thereafter, in step S34, the reaction solution is allowed to stand for 12 hours or more at room temperature, so as to produce a ZnS-*listeria* apoferritin complex. At this point, the pH is set to approximately 4.0 or more and 9.0 or less.

The end concentrations of the reagents are not limited those mentioned above. Exemplified ranges of the concentrations of the respective reagents are listed in FIG. 14B. However, even when the end concentration of the *listeria* apoferritin in the reaction solution is out of the range from 0.3 mg/mL to 1 mg/mL, a ZnS-*listeria* apoferritin complex can be produced. Also, the concentration of ammonium acetate is not limited to 40 mM.

The ZnS-*listeria* apoferritin complex produced by this method includes 12 monomer sub-units of *listeria* apoferritin, and includes a shell having a cavity inside and a nanoparticle of ZnS formed within the cavity. The diameter of the nanoparticle is approximately 5 nm or less.

Modification of Embodiment 4

FIG. 14C is a diagram for showing the conditions for producing a compound semiconductor-*listeria* apoferritin according to a modification of Embodiment 4.

In a method of this modification, an ammonium acetate solution, a zinc acetate solution, ammonia water and a *listeria* apoferritin solution are mixed in step S31 of FIG. 14A so as to attain end concentrations shown in FIG. 14C. At this point, the reaction temperature is set to 0° C. or more and 15° C. or less. Particularly, the temperature is preferably approximately 4° C. Also, the concentration of the cadmium acetate solution is preferably higher than that in Embodiment 3.

Next, after allowing the reaction solution to stand for 10 minutes in step S32, thioacetate acid is added to the reaction solution so as to attain a concentration shown in FIG. 14C. At this point, the concentration of the thioacetic acid is preferably hither than in Embodiment 4.

Next, in step S34, the reaction solution is allowed to stand for 12 hours or more at a temperature of 0° C. through 15° C., so as to produce a ZnS-*listeria* apoferritin complex.

In this method, the forming ratio of a ZnS nanoparticle in *listeria* apoferritin can be improved to approximately 100%. It seems that ZnS is gradually precipitated when the temperature is lowered and the zinc concentration is increased at the same time of the production of the CdS-*listeria* apoferritin complex so as to suppress the precipitation outside the *listeria* apoferritin. Therefore, it is presumed that the forming ratio of the nanoparticle within the *listeria* apoferritin is improved.

According to this method, a ZnS nanoparticle can be more definitely produced than in the method of Embodiment 4. Therefore, the cost for producing the nanoparticle can be lowered.

Embodiment 5

In Embodiment 5 of the invention, a method for producing a nanoparticle-protein complex including a compound semiconductor by using recombinant apoferritin prepared by the gene recombination technology will be described.

As described above, the commercially available apoferritin used in the method of Embodiment 1 or 2 is a composite substance of two kinds of monomer sub-units, that is, the H sub-unit and the L sub-unit. The amino acid sequence of the L sub-unit is shown in Sequence List No. 1. It is said that 8 residues from the N-terminal of naturally present apoferritin are deleted through processing in vivo. A part of the 8 residues is protruded from the outer surface of the apoferritin, and when this part is lost, the state of surface charge of the apoferritin seems to change. In a method of this embodiment, a nanoparticle-protein complex is produced by using recombinant apoferritin including an L sub-unit alone in which 7 residues out of the 8 residues of the N-terminal excluding methionine present at the top of the amino acid sequence are deleted.

First, an L sub-unit is prepared by the gene recombination technology by deleting second through eighth amino acids (from the N-terminal) of horse L-apoferritin. Specifically, a DNA for coding an L sub-unit in which the second through eighth amino acids are deleted is introduced into an expression vector, which is used for transforming *Escherichia coli* (*E. coli*), and thus, recombinant apoferritin including merely the L sub-unit in which the N-terminal amino acids are deleted is obtained. This recombinant apoferritin is hereinafter designated as "Fer8 apoferritin". The amino acid sequence of the Fer8 apoferritin is shown in Sequence List No. 2.

Next, a CdS-Fer8 apoferritin complex is produced in a similar manner to that employed in using commercially available apoferritin (see Embodiment 1). Thus, the CdS-Fer8 apoferritin complex can be obtained at high yield. However, when the Fer8 apoferritin is used, a core of CdS can be formed with pH of a reaction solution set to a range from 4.0 to 9.5.

Figure 15:
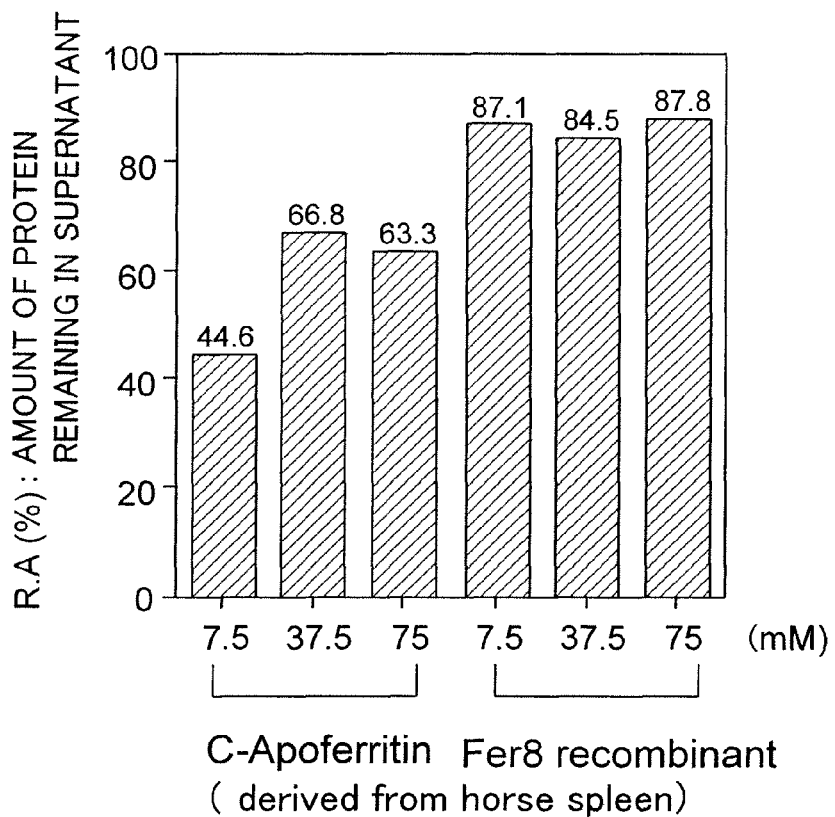
FIG. 15 is a diagram for showing the amounts of protein remaining in a supernatant of a reaction solution in using commercially available apoferritin (with no deletion) and Fer8 apoferritin.

FIG. 15 is a diagram for showing the amounts of proteins remaining in supernatants of reaction solutions in using commercially available apoferritin (C-apoferritin) and the Fer8 apoferritin. The measurement result is obtained by centrifuging a reaction solution at 12000 rpm for approximately 10 minutes after producing a nanoparticle-apoferritin complex and measuring a protein remaining in the thus obtained supernatant.

As a result, as shown in FIG. 15, a larger amount of protein remains in the supernatant in any of the ammonia concentrations in using the Fer8 apoferritin than in using the commercially available horse spleen-derived apoferritin. This means that a ratio of precipitation of aggregation of the apoferritin in the reaction solution is lower in using the Fer8 apoferritin than in using the commercially available apoferritin. Accordingly, when the Fer8 apoferritin is used, the CdS-apoferritin complex seems to be obtained at higher yield than in using the commercially available apoferritin.

Figure 16:
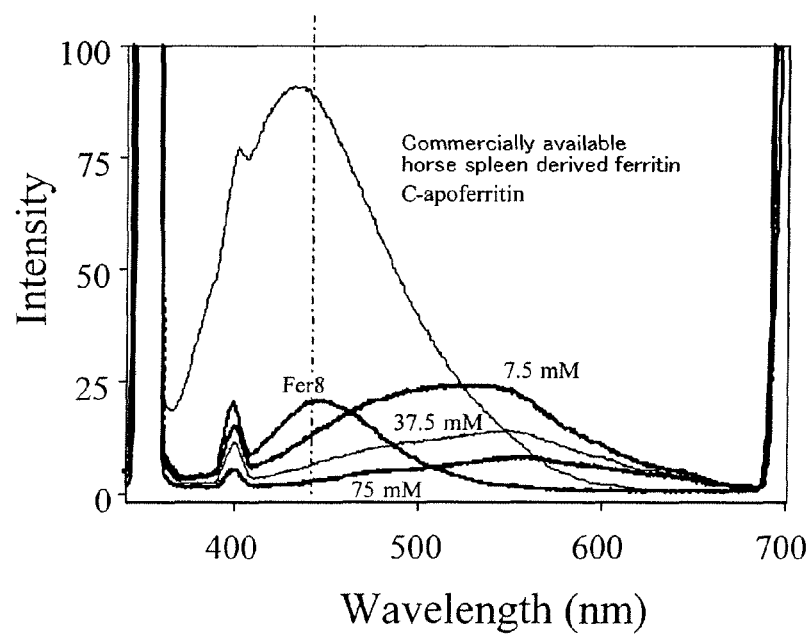
FIG. 16 is a diagram for showing fluorescence spectra of a CdS-Fer8 apoferritin complex obtained when the ammonia concentration in a reaction solution is 7.5 mM, 37.5 mM and 75 mM.

Next, FIG. 16 is a diagram for showing fluorescence spectra of CdS-Fer8 apoferritin complexes obtained when the ammonia concentration in the reaction solution is 7.5 mM, 37.5 mM and 75 mM. In FIG. 16, the fluorescence spectrum of the commercially available horse spleen-derived apoferritin alone is indicated as "C-apoferritin" and the fluorescence spectrum of the Fer8 apoferritin alone is indicated as "Fer8". It is understood from FIG. 16 that the CdS-Fer8 apoferritin emits fluorescence in the vicinity of a wavelength of 500 through 600 nm in response to excitation light. Also, it is understood through the comparison of the results of the commercially available apoferritin alone and the Fer8 apoferritin alone that fluorescence derived from the Fer8 apoferritin has smaller intensity than fluorescence derived from the commercially available apoferritin. Accordingly, in the CdS-Fer8 apoferritin complex, the fluorescence derived from CdS is less affected by the fluorescence derived from the Fer8 apoferritin.

Figure 17:
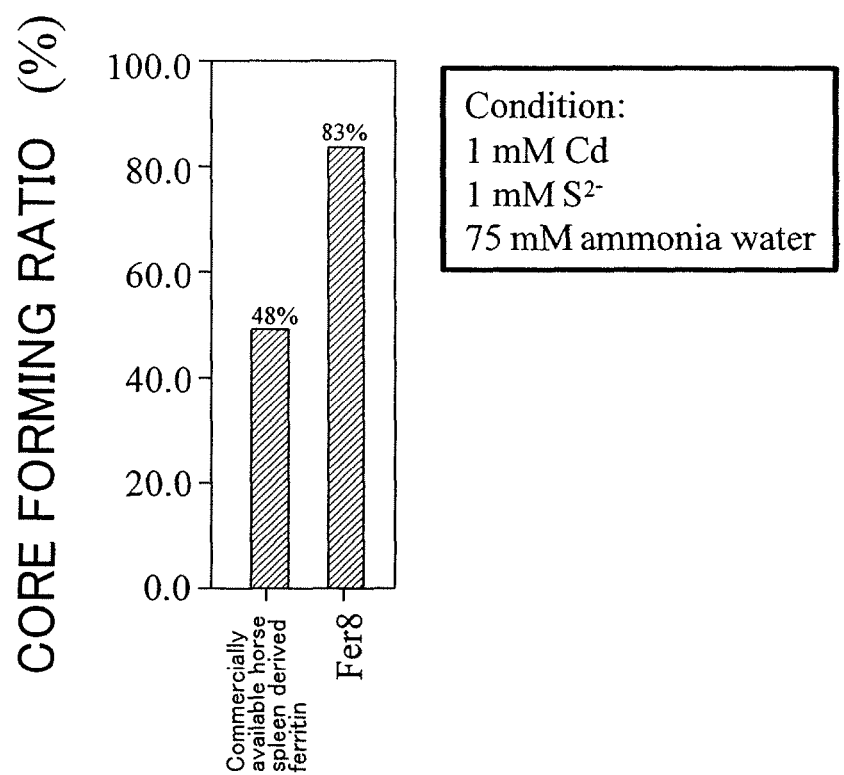
FIG. 17 is a diagram for showing comparison in a core forming ratio between commercially available apoferritin and Fer8 apoferritin.

Furthermore, FIG. 17 is a diagram for showing comparison in the ratio of forming a core within apoferritin between the commercially available apoferritin and the Fer8 apoferritin. In this test, the Cd concentration in a reaction solution is 1 mM, the $S^{2-}$ concentration is 1 mM and the ammonia concentration is 75 mM.

As is understood from FIG. 17, the ratio of forming a core of CdS within the apoferritin is higher in using the Fer8 apoferritin than in using the commercially available apoferritin. Accordingly, the yield of the CdS-apoferritin complex can be largely improved by using the Fer8 apoferritin.

Moreover, since the Fer8 apoferritin is secured for supply in a large amount owing to the gene recombination technology, nanoparticles of CdS can be produced at low cost.

As described so far, when the Fer8 apoferritin is used, a nanoparticle of CdS can be formed inexpensively at high yield, and a CdS-apoferritin complex in which the fluorescence derived from the CdS is less affected by the fluorescence derived from the protein can be produced. Accordingly, the method of this embodiment is more preferably employed for application of the complex to a semiconductor device or the like.

Although a nanoparticle of CdS is formed within the Fer8 apoferritin in this embodiment, a nanoparticle of ZnS can be formed within the Fer8 apoferritin in a similar manner to the method of Embodiment 2.

Also, with respect to *listeria* apoferritin, there is a possibility that the core forming ratio can be improved by deleting a part of the N-terminal. Such *listeria* apoferritin can be produced in a large amount by the gene recombination technology using *E. coli* or the like.

Embodiment 6

In embodiments described below, exemplified application of a compound semiconductor-apoferritin (or *listeria* apoferritin) complex will be described.

—Structure and Function of Semiconductor Device—

Figure 18:
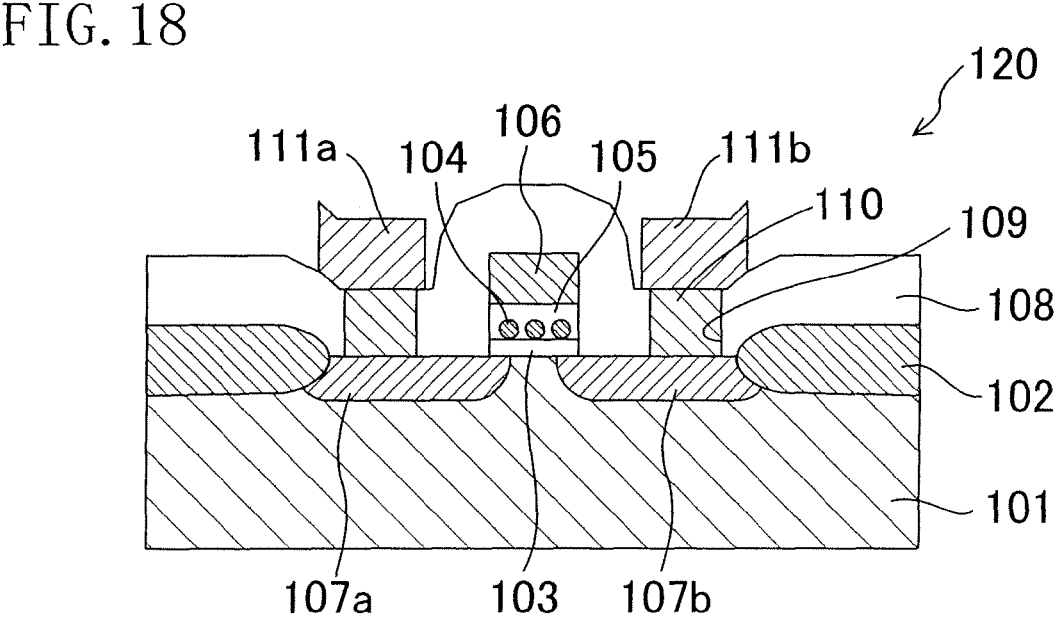
FIG. 18 is a cross-sectional view of a semiconductor device according to Embodiment 6 of the invention.

FIG. 18 is a cross-sectional view of a semiconductor device according to Embodiment 6 of the invention. The semiconductor device shown in this drawing is a nonvolatile memory cell using a quantum dot of a compound semiconductor.

As shown in FIG. 18, the semiconductor device 120 of this embodiment includes a semiconductor substrate 101 made of a semiconductor of a first conductivity type such as Si, an isolation insulating film 102 surrounding an active region in a surface portion of the semiconductor substrate 101, a tunnel insulating film 103 made of $SiO_2$ or the like and formed on the active region of the semiconductor substrate 101, nanoparticles 104 of a compound semiconductor and disposed above and spaced from the tunnel insulating film 103, an insulating film 105 made of $SiO_2$ or the like and provided on the tunnel insulating film 103 for burying the nanoparticles 104, a control gate (gate electrode) 106 made of a conductor such as Al and provided on the insulating film 105, a source region 107a and a drain region 107b (impurity diffusion layers) including an impurity of a second conductivity type and provided in portions of the semiconductor substrate 101 disposed on both sides of the control gate 106, an interlayer insulating film 108 provided over the substrate, contact holes 109 formed in the interlayer insulating film 108, and Al interconnections 111a and 111b respectively connected to the source region 107a and the drain region 107b through plugs filled in the contact holes 109. The tunnel insulating film 103 has a thickness of, for example, approximately 1.5 nm or more and 4 nm or less, and the insulating film 105 has a thickness of, for example, approximately 17 nm.

Also, each nanoparticle 104 is in a spherical shape with a diameter of approximately 7 nm. A distance between the centers of the nanoparticles 104 is approximately 12 nm, and the nanoparticles are two-dimensionally arranged on the tunnel insulating film 103. The nanoparticles 104 are made of, for example, CdS or ZnS.

It is assumed in the exemplified semiconductor device of FIG. 18 that the source region 107a and the drain region 107b include an n-type impurity in a high concentration and that the semiconductor substrate 101 includes a p-type impurity.

In the semiconductor device of this embodiment, two kinds of drain current-gate voltage characteristics are exhibited depending upon whether or not charge is held by the nanoparticles 104. Specifically, in the semiconductor device of this embodiment, different drain current-gate voltage characteristics are exhibited between a state where electrons have been injected into the nanoparticles 104 and a state where electrons have been drawn from the nanoparticles 104. Therefore, when the semiconductor device of this embodiment is operated as follows, it can function as a nonvolatile memory cell:

First, in injecting electrons into the nanoparticles 104, a positive voltage is applied to the control gate 106. Thus, the electrons are injected into the nanoparticles 104 by direct tunneling through the tunnel insulating film 103. On the contrary, in drawing electrons from the nanoparticles 104, a negative voltage is applied to the control gate 106. When the state where the electrons have been injected into the nanoparticles 104 or the state where they are not is allowed to correspond to information of "1" or "0", the information can be written in the aforementioned manner. In reading the information, a drain current obtained under application of a given gate voltage is read by using a sense amplifier (not shown).

Although the diameter of each nanoparticle 104 of the semiconductor device of this embodiment is approximately 7 nm, a nanoparticle with smaller diameter may be used. A nanoparticle with a diameter smaller than 7 nm can be produced, as described in Embodiment 1, by changing an ammonia concentration in a reaction solution in producing a CdS-apoferritin complex.

—Method for Fabricating Semiconductor Device—

FIGS. 19A through 19F are cross-sectional views for explaining a method for fabricating the semiconductor device of this embodiment.

First, as shown in FIG. 19A, metal ions and sulfide ions 135 are introduced through a three-fold symmetric channel 130 into a basket-shaped protein such as apoferritin 132 or *listeria* apoferritin by the method described in any of Embodiments 1 through 4, so as to form nanoparticles of CdS or ZnS.

Next, as shown in FIG. 19B, after forming a $SiO_2$ film 103a with a thickness of 1.5 nm or more and 4 nm or less through thermal oxidation on a semiconductor substrate 101 including a p-type impurity in a concentration of approximately 1 through $5 \times 10^{16}$ cm$^{-3}$, an isolation insulating film 102 is formed by a LOCOS method. The isolation insulating film 102 may be formed by an STI (shallow trench isolation) method. Next, the surfaces of the isolation insulating film 102 and the $SiO_2$ film 103a on the substrate are modified with amino groups by using a methoxy silane compound such as 3-(2-aminoethyl amino)propyl-trimethoxy silane (APTMS). Thereafter, nanoparticle-apoferritin complexes 137 prepared in the above-described procedure are two-dimensionally arranged on the isolation insulating film 102 and the $SiO_2$ film 103a. The nanoparticle-apoferritin complexes 137 are arranged on the substrate by, for example, a method described in Japanese Laid-Open Patent Publication No. 11-45990.

Next, as shown in FIG. 19C, the apoferritin 132 (a portion corresponding to the shell) and the 3-(2-aminoethyl amino) propyl-trimethoxy silane (APTMS) molecules are removed by irradiating the substrate with ultraviolet (UV) at intensity of 110 W for 10 minutes in the presence of ozone. Thus, nanoparticles 104 with a diameter of approximately 7 nm two-dimensionally arranged at intervals between their centers of approximately 12 nm remain on the substrate. In this procedure, in an atmosphere including ozone, the substrate is irradiated with UV of wavelengths of 253.7 nm and 184.9 nm at intensity of 110 W for 40 minutes. This procedure is performed at 115° C. for removing moisture. It is noted that an organic substance such as the apoferritin 132 can be removed also through oxygen plasma processing performed at room temperature or annealing performed at 400° C. in a nitrogen atmosphere.

Subsequently, as shown in FIG. 19D, a $SiO_2$ film 105a with a thickness of 17 nm sufficient for burying the nanoparticles 104 is formed on the isolation insulating film 102 and the $SiO_2$ film 103a (over the whole substrate) by sputtering. The sputtering of this procedure is performed by using, for example, $SiO_2$ as a target at room temperature at a pressure of 4.7 through $5.3 \times 10^{-1}$ Pa with RF output set to 200 W, an argon flow set to 16 sccm (mL/min. at 0° C. and 101.3 kPa) and an oxygen flow set to 4 sccm for 4 minutes and 30 seconds. It is noted that the $SiO_2$ film 105a may be formed by CVD.

Next, as shown in FIG. 19E, an Al film is deposited on the substrate. Subsequently, the $SiO_2$ film 103a, the insulating film 105 and the Al film are patterned by using a photoresist mask Pr1, so as to form a tunnel insulating film 103, an insulating film 105 working as an inter-electrode insulating film and a control gate 106 of Al. Thereafter, n-type impurity ions are implanted by using the photoresist mask and the control gate 106 as a mask, so as to form a source region 107a and a drain region 107b.

Thereafter, in a procedure shown in FIG. 19F, known methods are employed for forming an interlayer insulating film 108, forming a contact hole 109 in the interlayer insulating film 108, forming a tungsten plug 110 by filling the contact hole 109 with tungsten, and forming Al interconnections 111a and 111b.

In the aforementioned manner, the semiconductor device of this embodiment can be fabricated. As described in this embodiment, a semiconductor memory utilizing a characteristic of a quantum dot can be realized by using the compound semiconductor-protein complex prepared by the method of any of Embodiments 1 through 4.

Embodiment 7

As Embodiment 7 of the invention, a method for using a compound semiconductor-protein complex of this invention as a fluorescence label will be described.

—First Method—

FIGS. 20A through 20G are diagrams for explaining a first fluorescence labeling method of this embodiment. In this case, a method for fluorescence labeling a target substance by using a compound semiconductor-protein complex will be described.

Figure 20:
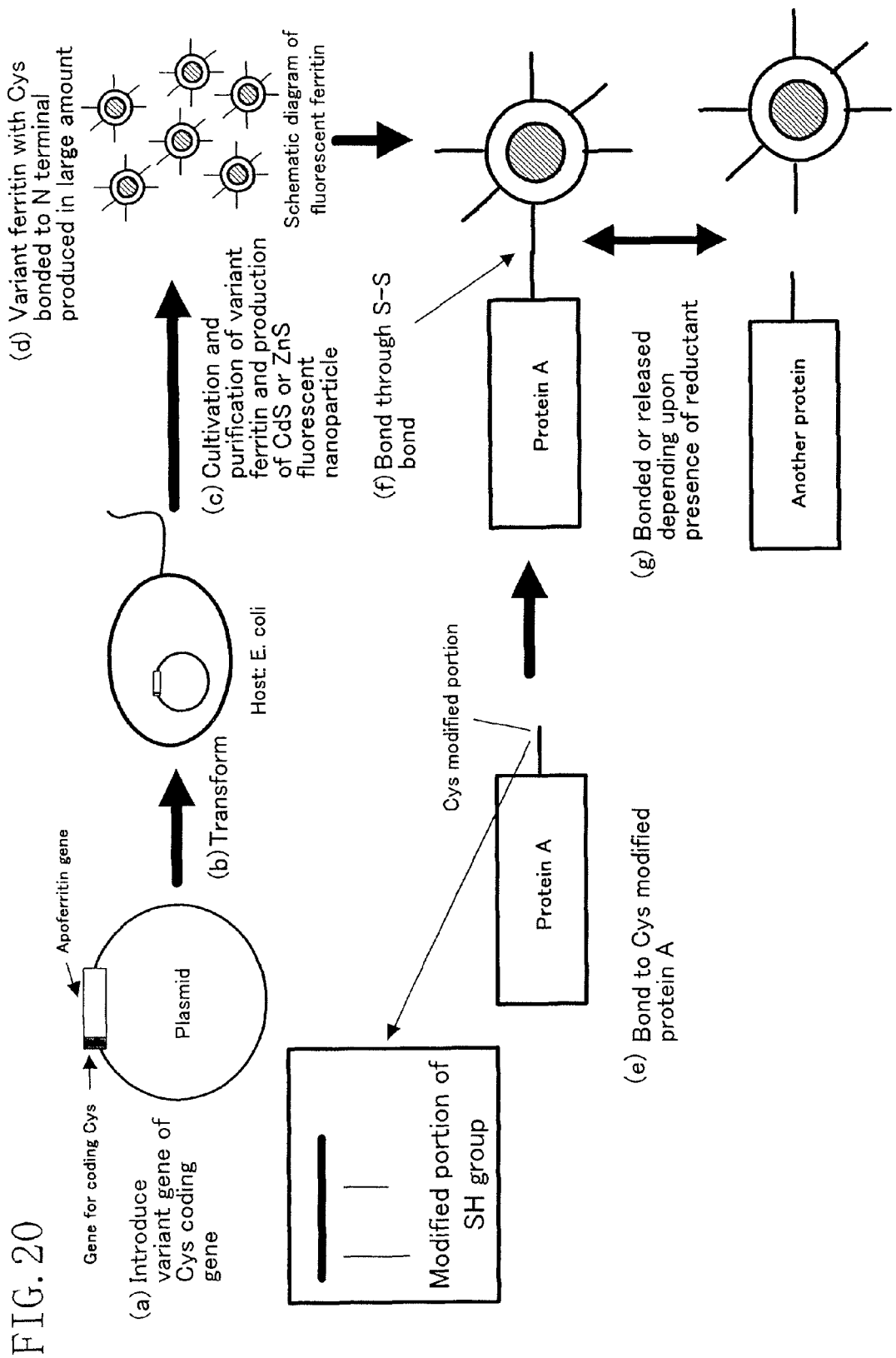
FIGS. 20A through 20G are diagrams for explaining a first fluorescence labeling method according to Embodiment 7 of the invention.

First, as shown in FIG. 20A, an apoferritin DNA having a sequence for coding cysteine (mentioned as "Cys" in the drawing) in a top portion (on the side of 5') is integrated into a plasmid. This plasmid is an expression vector.

Next, as shown in FIG. 20B, the thus prepared plasmid is introduced into E. coli used as a host, so as to transform the E. coli.

Subsequently, as shown in FIGS. 20C and 20D, the transformed E. coli is cultured, so as to extract and purify variant apoferritin (apoferritin having Cys at the N-terminal) produced in the bacteria body. Thereafter, a nanoparticle of CdS or ZnS is formed within the purified variant apoferritin by the method described in Embodiment 1 or 2. Thus, a complex of the nanoparticle and the apoferritin having Cys at the N-terminal can be produced.

On the other hand, as shown in FIG. 20E, Cys is substituted for an amino acid residue exposed on the surface of a substance to be labeled (such as a protein A shown in the drawing). Alternatively, Cys or an SH group is substituted for or added to a surface exposed portion of a protein to be labeled. It is noted that a target substance is not limited to a protein but may be any substance as far as an SH group can be introduced. For example, a DNA or a high molecular compound such as a polymer can be used as the target substance.

Next, as shown in FIG. 20F, a solution including the protein A and a solution including the nanoparticle-variant apoferritin complex are mixed. Thus, the Cys of the protein A and the Cys of the nanoparticle-variant apoferritin complex together form a S—S bond (a disulfide bond), so as to bond the protein A and the nanoparticle variant apoferritin complex to each other. Since the nanoparticle included in the nanoparticle-variant apoferritin complex emits fluorescence through excitation with excitation light of a wavelength of, for example, 350 nm, the protein A can be detected by using this fluorescence. In this manner, the target protein can be fluorescence labeled. In the case where the target substance is a substance other than a protein, the SH group added to the target substance and the Cys of the nanoparticle-variant apoferritin complex are made to together form a S—S bond. It is noted that the S—S bond can be easily cut by adding a reductant as shown in FIG. 20G.

According to this method, an arbitrary protein can be fluorescence labeled, and in addition, when a nanoparticle-variant apoferritin complex having a different diameter of a nanoparticle is used, the fluorescence wavelength of the labeled protein can be changed. In this manner, the compound semiconductor-protein complex of this invention can be used as a marker for a biogenic substance or the like.

Apart from the method described above, the compound semiconductor-protein complex of this invention can be used in a fluorescence labeling method using an avidin-biotin bond or an antigen-antibody reaction.

Also, in the method of this embodiment, *listeria* apoferritin can be used instead of apoferritin.

Furthermore, as described above, not only a protein but also any substance having an SH group or modifiable with an SH group, such as a DNA, an antigen, virus or a high molecular compound like a polymer, can be fluorescence labeled.

—Second Method—

Figure 21:
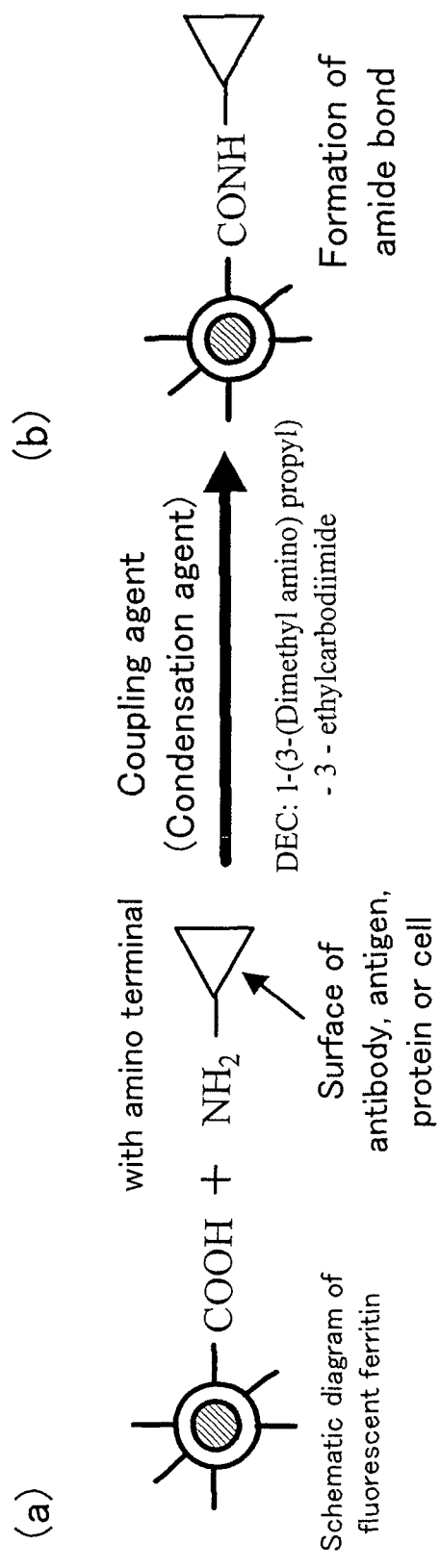
FIGS. 21A and 21B are diagrams for explaining a second fluorescence labeling method of Embodiment 7.

FIGS. 21A and 21B are diagrams for explaining a second fluorescence labeling method of this embodiment.

First, as shown in FIG. 21A, a nanoparticle-apoferritin complex is produced by the method of Embodiment 1 or 2. Then, a solution including the nanoparticle-apoferritin complex and a solution including a target to be labeled (a target biogenic substance such as a protein including an antibody and an antigen, or a cell) are mixed. Subsequently, when a coupling agent such as DEC (1-(3-(dimethyl amino)propyl)-3-ethylcarbodiimide) is added to the thus obtained reaction solution, a condensation reaction is caused between a carboxyl group present on the outer surface of the apoferritin and an amino terminal of the labeling target, resulting in forming an amide bond as shown in FIG. 21B. Thus, a labeling target to which the nanoparticle-apoferritin complex is bonded can be prepared. Since a nanoparticle included in the nanoparticle-apoferritin complex emits fluorescence against excitation light of a wavelength of, for example, 350 nm, the labeling target can be easily observed.

It is noted that the nanoparticle may be formed within apoferritin after bonding the apoferritin to a labeling target by adding the labeling target and a coupling agent to an apoferritin solution.

In this method, the target substance may be, apart from a protein or a cell, a substance having an amino group such as a DNA, a polymer or a carbon nano-horn, or a substance chemically modifiable with an amino group.

Embodiment 8

As Embodiment 8 of the invention, a method for fluorescence labeling a substrate will be described.

A Ti-recognition peptide for recognizing and bonding titanium (Ti) or the like has been disclosed in a document and the like (Kenichi Sano, et al., Small, No. 8-9, pp. 826-832 (2005)). This Ti-recognition peptide includes 6 amino acid residues, that is, Arg-Lys-Leu-Pro-Asp-Ala, and has a property to bond to Ti, Si or the like. In the fluorescence labeling method of this embodiment, a Ti-recognition peptide is used for providing a nanoparticle-apoferritin complex in a desired position on a substrate. The procedures of the method will now be described.

Figure 22:
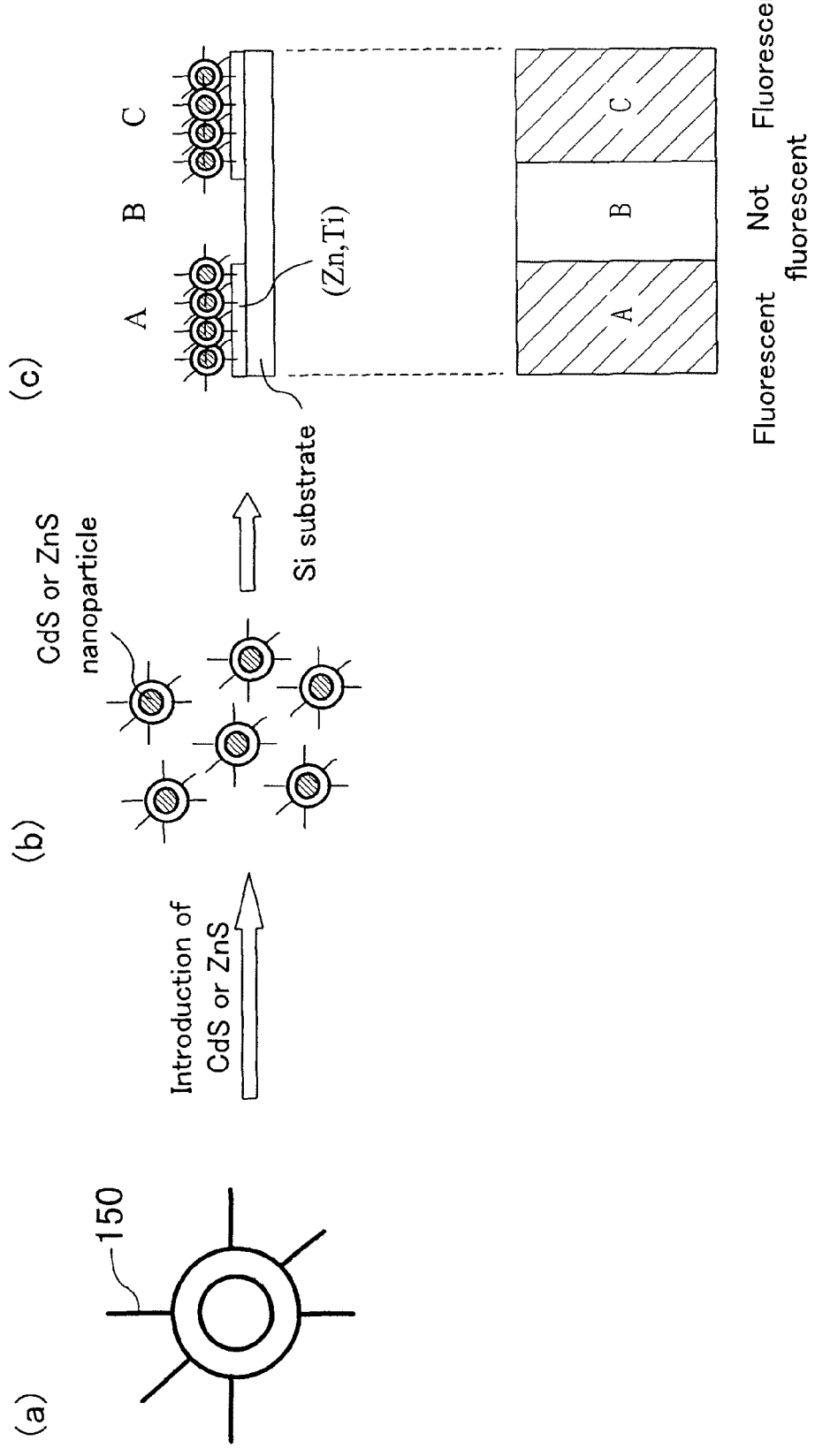
FIGS. 22A through 22C are diagrams for showing the outline of a fluorescence labeling method for a substrate according to Embodiment 8 of the invention.

FIGS. 22A through 22C are diagrams for showing the outline of the fluorescence labeling method for a substrate according to Embodiment 8 of the invention.

First, as shown in FIG. 22A, a Ti-recognition peptide 150 is provided on the outer surface of apoferritin. The Ti-recognition peptide 150 may be bonded to the outer surface of the apoferritin by using a coupling agent or the like, or is introduced into the N-terminal of the apoferritin by the gene recombination technology preferably for the productivity. Specifically, a DNA for coding the apoferritin and having, on the upstream side (the 5' side), a DNA for coding the Ti-recognition peptide 150 is introduced into an expression vector, and the resultant vector is introduced into *E. coli* or the like. Within this *E. coli*, recombinant apoferritin in which the Ti-recognition peptide 150 is added to the N-terminal side is produced in a large amount. Next, the recombinant apoferritin is extracted from the bacteria body and purified. The recombinant apoferritin can be purified in the form of aggregation of monomer sub-units. Since the N-terminal of a monomer sub-unit is protruded from the outer surface of the apoferritin, the Ti-recognition peptide added to the N-terminal side is also protruded from the outer surface of the recombinant apoferritin. It is noted that the amino acid sequence of the monomer sub-unit of the recombinant apoferritin is shown in Sequence List No. 3.

Next, as shown in FIG. 22B, a nanoparticle of CdS or ZnS is formed within the recombinant apoferritin. This procedure is performed in the same manner as in the method of Embodiment 1 or 2.

Subsequently, as shown in FIG. 22C, the thus obtained nanoparticle-recombinant apoferritin complex is disposed on a substrate. At this point, a Ti film is previously formed on a region of the substrate where the nanoparticle-recombinant apoferritin complex is desired to be disposed. When the resultant substrate is placed in an aqueous solution including the nanoparticle-recombinant apoferritin complex, the nanoparticle-recombinant apoferritin complex is bonded to merely the portion of the substrate where the Ti film has been formed. Since CdS or ZnS emits fluorescence when excited by UV or the like, the fluorescence is observed merely in the portion of the substrate where the nanoparticle-recombinant apoferritin complex is disposed.

In this manner, according to the method of this embodiment, a nanoparticle-recombinant apoferritin complex can be disposed in accordance with a pattern of a Ti film formed on a substrate, and therefore, any of various fluorescence patterns can be drawn on a substrate.

Furthermore, when nanoparticle-recombinant apoferritin complexes having different diameters of nanoparticles are disposed in different regions on a substrate, different fluorescence can be obtained in the respective regions. Moreover, when a ZnS-recombinant apoferritin complex for emitting blue light and a CdS-recombinant apoferritin complex for emitting red light are disposed in different regions on a substrate, a nano-fluorescence pattern or a nano-fluorescence letter can be created. Alternatively, since a nanoparticle of a compound semiconductor can be disposed in an arbitrary position on a substrate, a semiconductor device or an optical device more complicated than conventional devices can be fabricated.

Although a Ti-recognition peptide is added to the N-terminal of apoferritin derived from a horse spleen in this embodiment, even when the Ti-recognition peptide is added to the N-terminal of apoferritin derived from another organ or apoferritin derived from another animal, a nanoparticle can be provided in an arbitrary region on a substrate.

Furthermore, a similar effect can be attained by adding a Ti-recognition peptide to the N-terminal side of *listeria* apoferritin.

Embodiment 9

Figure 23:
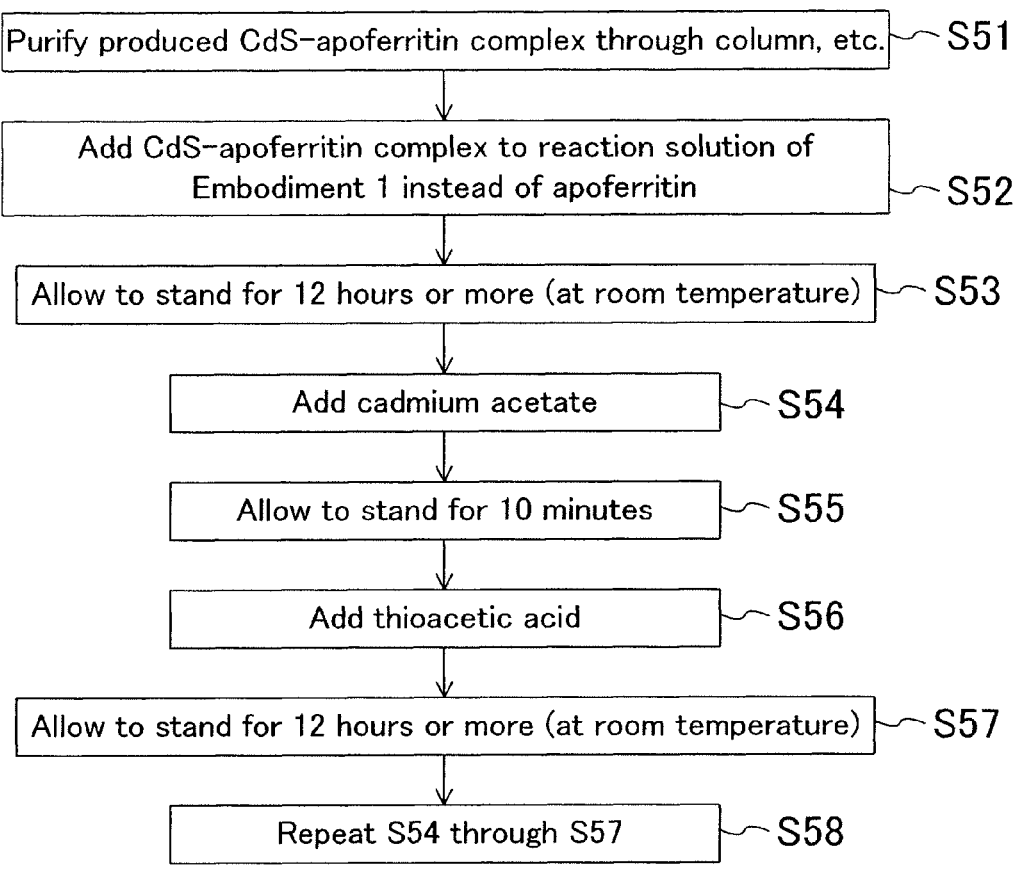
FIG. 23 is a flowchart of a method for producing a compound semiconductor-apoferritin complex according to Embodiment 9 of the invention.

FIG. 23 is a flowchart of a method for producing a compound semiconductor-apoferritin complex according to Embodiment 9 of the invention. In this embodiment, a method for forming a nanoparticle of CdS within apoferritin will be described.

First, in step S51 of FIG. 23, after forming a CdS-apoferritin complex by the method of Embodiment 1, the CdS-apoferritin complex is purified by using a column or the like.

Next, in step S52, the purified CdS-apoferritin complex is added again to a reaction solution with a composition shown in FIG. 2B. At this point, the CdS-apoferritin complex is used instead of apoferritin, and its concentration is preferably the same as that of apoferritin, namely, 0.3 mg/mL through 1.0 mg/mL. Thereafter, in step S53, the resultant reaction solution is allowed to stand for 12 hours or more at room temperature.

Next, in step S54, cadmium acetate is added to the reaction solution so as to attain an end concentration of 1 mM, and in step S55, the resultant reaction solution is allowed to stand for 10 minutes at room temperature.

Subsequently, in step S56, thioacetic acid is added to the reaction solution so as to attain an end concentration of 1 mM. Thereafter, in step S57, the reaction solution is allowed to stand for 12 hours or more at room temperature.

Next, in step S58, the procedures of steps S54 through S57 are repeated.

In this manner, a nanoparticle formed within the apoferritin can be further grown.

Figure 24:
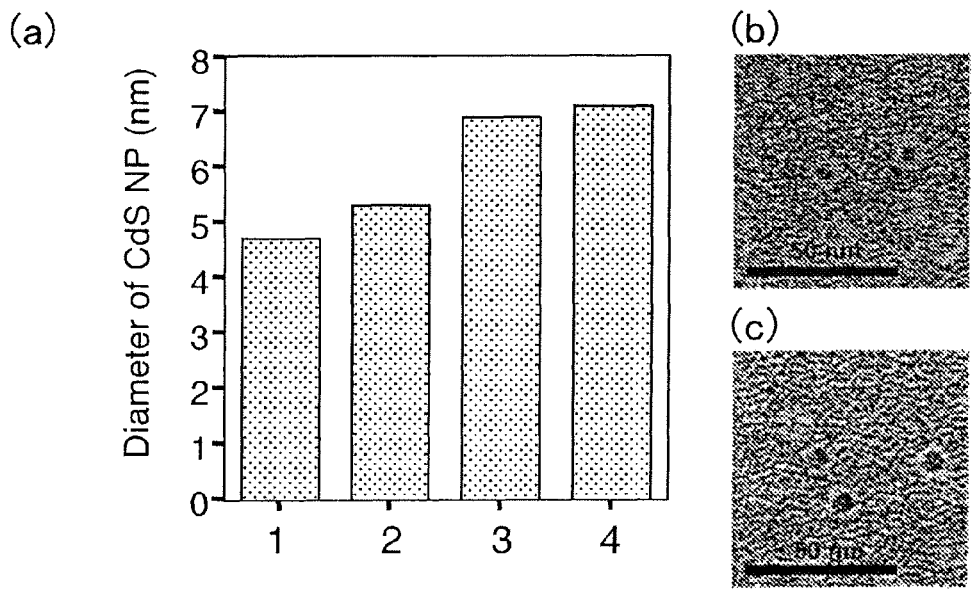
FIG. 24A is a diagram for showing a diameter of a CdS nanoparticle produced by the method of Embodiment 9.
FIG. 24B is a TEM photograph of a CdS-apoferritin complex produced by the method of Embodiment 1 and FIG. 24C is a TEM photograph of the CdS-apoferritin complex produced by the method of Embodiment 9.

FIG. 24A is a diagram for showing the diameter of a CdS nanoparticle formed by using 7.5 mM ammonia water in the method of this embodiment, FIG. 24B is a TEM photograph of the CdS-apoferritin complex produced by the method of Embodiment 1 and FIG. 24C is a TEM photograph of the CdS-apoferritin complex produced by the method of this embodiment.

In FIG. 24A, "Condition 1" corresponds to the nanoparticle formed by the method of Embodiment 1, "Condition 2" corresponds to a nanoparticle formed by adding 1 mM cadmium and 1 mM thioacetic acid once after the purification of the CdS-apoferritin complex, "Condition 3" corresponds to a nanoparticle formed by adding 1 mM cadmium and 1 mM thioacetic acid twice after the purification of the CdS-apoferritin complex, and "Condition 4" corresponds to a nanoparticle formed by adding 1 mM cadmium and 1 mM thioacetic acid three times after the purification of the CdS-apoferritin complex.

It is understood from the this result that the size of the CdS nanoparticle formed within the apoferritin can be increased by alternately adding cadmium and thioacetic acid after forming the CdS-apoferritin complex once. In the case where cadmium and thioacetic acid are added three times after the purification of the CdS-apoferritin complex, the diameter of the CdS nanoparticle is approximately 7 nm, which is substantially the same as the size of the cavity of the apoferritin. Also, according to the method of this embodiment, variation in the diameter of CdS nanoparticles can be reduced by repeating the addition of cadmium and thioacetic acid.

In the method of this embodiment, the time for allowing the reaction solution to stand in step S55 is not limited to 10 minutes. Also, the concentration of cadmium acetate added in step S54 is not limited to 1 mM, and the concentration of thioacetic acid added in step S56 is not limited to 1 mM.

Furthermore, the aforementioned reaction can be caused at 0 through 15° C.

Moreover, a ZnS-apoferritin complex, a CdS-*listeria* apoferritin complex or a ZnS-*Listeria* apoferritin complex can be produced by a method similar to the method of this embodiment.

For example, in producing a ZnS-apoferritin complex, a ZnS-apoferritin complex produced by the method of Embodiment 2 is purified to be added to a reaction solution. Subsequently, 1 mM zinc acetate and 1 mM of thioacetic acid are successively added to the reaction solution. Thereafter, zinc acetate and thioacetic acid are alternately added so as to grow a ZnS nanoparticle. Alternatively, in producing a CdS-*listeria* apoferritin complex or a ZnS-*listeria* apoferritin complex, the apoferritin is replaced with *listeria* apoferritin in the aforementioned method.

In this manner, nanoparticles of a compound semiconductor having a uniform size at a high level can be formed.

It is noted that the procedures of steps S51 through S58 may be performed by using a CdS-apoferritin complex produced by a method other than the method of Embodiment 1.

INDUSTRIAL APPLICABILITY

As described so far, a compound semiconductor-protein complex produced by the method of this invention is applicable to various uses including a semiconductor device utilizing a quantum dot and fluorescence labeling of biogenic substances.

The invention claimed is:

1. A method for producing a nanoparticle-protein complex comprising the steps of:
   (a) forming an ammonium complex of a metal in an aqueous solution; and
   (b) mixing a solution of a protein having a cavity inside and thioacetic acid in the aqueous solution, whereby forming a nanoparticle made of a sulfide of the metal within the cavity of the protein,
   wherein the protein is apoferritin, *listeria* apoferritin (*listeria* Dps) or a recombinant thereof, the metal is Cd or Zn, and the pH of the mixed solution in step (b) is set in the range between about 9.0 and about 4.0.

2. The method for producing a nanoparticle-protein complex of claim 1, wherein a solution including acetic acid ions and ammonium ions, an acetate solution of the metal and ammonia water are mixed in the step (a).

3. The method for producing a nanoparticle-protein complex of claim 2, wherein a nanoparticle with a different diameter is formed in accordance with an ammonia concentration in the aqueous solution in the step (b).

4. The method for producing a nanoparticle-protein complex of claim 1,
   wherein the protein is *listeria* apoferritin or a recombinant of *listeria* apoferritin, and the steps (a) and (b) are performed at a temperature of 0° C. or more and 15° C. or less.

5. The method for producing a nanoparticle-protein complex of claim 1, further comprising the steps of:
   (c) purifying a complex of the nanoparticle and the protein obtained in the step (b);
   (d) mixing a solution including the complex of the nanoparticle and the protein purified in the step (c) and a solution including the metal;
   (e) adding thioacetic acid to a mixed solution obtained in the step (d) for growing the nanoparticle formed within the protein; and
   (f) growing the nanoparticle by repeating a procedure for alternately adding the solution including the metal and the thioacetic acid to the mixed solution after the step (e).

6. A method for producing a nanoparticle-protein complex comprising the steps of:
   (a) preparing a solution including a complex of a protein having a cavity inside and a nanoparticle made of a sulfide of a metal and formed within the cavity;
   (b) adding a solution including the metal to the solution including the complex of the nanoparticle and the protein;
   (c) growing the nanoparticle by adding thioacetic acid to the solution including the complex of the nanoparticle and the protein after the step (b); and
   (d) growing the nanoparticle by repeating the step (b) and the step (c),
   wherein the protein is apoferritin, *listeria* apoferritin (*listeria* Dps) or a recombinant thereof, the metal is Cd or Zn, and the pH of the solution in step (c) is set in the range between about 9.0 and about 4.0.

7. A fluorescence labeling method comprising the steps of:
   (a) forming an ammonium complex of Cd or Zn in an aqueous solution;
   (b) mixing a solution of a protein having a cavity inside and thioacetic acid in the aqueous solution for forming within the cavity fluorescently active CdS or ZnS nanoparticle, producing a nanoparticle-protein complex; and
   (c) labeling a target substance by allowing the nanoparticle-protein complex to bond to the target substance,
   wherein the protein having a cavity inside is apoferritin, *listeria* apoferritin (*listeria* Dps) or a recombinant thereof, and the pH of the mixed solution in step (b) is set in the range between about 9.0 and about 4.0.

8. The fluorescence labeling method of claim 7, further comprising the steps of:
   (d) preparing first variant apoferritin or first variant *listeria* apoferritin having cysteine at an N-terminal before the step (c); and
   (e) modifying the target substance with a compound having an SH group before the step (c),
   wherein the first variant apoferritin or the first variant *listeria* apoferritin is bonded to the target substance through a disulfide bond in the step (c).

9. The fluorescence labeling method of claim 7, wherein the target substance has an amino group on an outer surface thereof, and an amide bond is formed through a condensation reaction caused, by using a coupling agent, between the amino group present on the outer surface of the target substance and a carboxyl group present on an outer surface of the apoferritin or the *listeria* apoferritin.

10. The fluorescence labeling method of claim 7, wherein the protein is second variant apoferritin having Ti-recognition peptide added to an N-terminal, and the target substance is a substrate having a Ti film formed on a part of a surface thereof.

11. The fluorescence labeling method of claim 10, further comprising, before the step (a), a step of preparing the second variant apoferritin by gene recombination technology.

12. A fluorescence labeling method comprising the steps of:
   (a) forming an ammonium complex of Cd or Zn in an aqueous solution;
   (b) bonding a protein having a cavity inside to a target substance; and
   (c) mixing a solution of the protein having a cavity inside and thioacetic acid in an aqueous solution for forming within the cavity fluorescently active CdS or ZnS nanoparticle, producing a nanoparticle-protein complex,
   wherein the protein having a cavity inside is apoferritin, *listeria* apoferritin (*listeria* Dps) or a recombinant thereof, and the pH of the mixed solution in step (c) is set to in the range between about 9.0 and about 4.0.

* * * * *